US008586504B2

(12) United States Patent
Wright et al.

(10) Patent No.: US 8,586,504 B2
(45) Date of Patent: Nov. 19, 2013

(54) HERBICIDAL COMPOSITIONS CONTAINING GLYPHOSATE AND A PYRIDINE ANALOG

(75) Inventors: Daniel R. Wright, St. Louis, MO (US); Joseph J. Sandbrink, Chesterfield, MO (US); Paul G. Ratliff, Olivette, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/404,861

(22) Filed: Feb. 24, 2012

(65) Prior Publication Data
US 2012/0157309 A1 Jun. 21, 2012

Related U.S. Application Data

(63) Continuation of application No. 10/829,572, filed on Apr. 22, 2004, now abandoned.

(60) Provisional application No. 60/496,031, filed on Apr. 22, 2003, provisional application No. 60/552,065, filed on Mar. 10, 2004.

(51) Int. Cl.
A01N 57/00 (2006.01)
A01N 25/00 (2006.01)

(52) U.S. Cl.
USPC ........................................ 504/116.1; 504/128

(58) Field of Classification Search
USPC .............................................. 504/116.1, 128
See application file for complete search history.

(56) References Cited

U.S. PATENT DOCUMENTS

| | | | |
|---|---|---|---|
| 3,799,758 A | 3/1974 | Franz | |
| 4,405,531 A | 9/1983 | Franz | |
| 4,692,184 A | 9/1987 | Lee | |
| 5,436,223 A | 7/1995 | Mulqueen et al. | |
| 5,565,409 A | 10/1996 | Sato et al. | |
| 5,703,015 A | 12/1997 | Berger et al. | |
| 5,834,006 A | 11/1998 | Smith et al. | |
| 5,883,048 A | 3/1999 | Morre et al. | |
| 5,998,332 A | 12/1999 | Sato et al. | |
| 6,063,733 A | 5/2000 | Berger et al. | |
| 6,228,807 B1 | 5/2001 | Kuchikata et al. | |
| 6,245,713 B1 | 6/2001 | Brinker et al. | |
| 6,277,788 B1 | 8/2001 | Wright | |
| 6,455,473 B2 | 9/2002 | Wright | |
| 6,569,809 B1 | 5/2003 | Sato et al. | |
| 6,579,831 B1 | 6/2003 | Harwell | |
| 6,677,276 B1 * | 1/2004 | Hacker et al. | 504/127 |
| 6,713,433 B2 | 3/2004 | Jimoh | |
| 6,723,681 B2 | 4/2004 | Hacker et al. | |
| 2002/0123430 A1 | 9/2002 | Xu et al. | |
| 2002/0155953 A1 * | 10/2002 | Brigance | 504/206 |
| 2003/0004063 A1 * | 1/2003 | Jimoh | 504/130 |
| 2004/0077499 A1 | 4/2004 | Graham et al. | |

FOREIGN PATENT DOCUMENTS

| | | |
|---|---|---|
| AU | 10073/92 B | 10/1992 |
| CA | 2340240 A1 | 2/2000 |
| EP | 0 808 569 A1 | 11/1997 |
| GB | 2 267 825 A | 12/1993 |
| WO | 99/00013 | 1/1999 |
| WO | 00/30452 | 6/2000 |
| WO | 00/64257 | 11/2000 |
| WO | 00/67571 | 11/2000 |
| WO | 01/35740 A2 | 5/2001 |
| WO | 02/21924 A2 | 3/2002 |

OTHER PUBLICATIONS

Exhibit PMH-17—Supplemental Labeling regarding Roundup Pro Herbicide by Monsanto, EPA Reg. No. 524-475 (Nov. 1995), 11 pages.
Exhibit PMH-18—Notice of Pesticide Registration issued on Oct. 5, 2000, 35 pages.
Exhibit PMH-19—EPA Application for Pesticide, ID No. 200405 (Sep. 1995), 33 pages.
Exhibit PMH-20—Documentation regarding Starmas Racun/Rumpai Herbicide (bears the year 2003), 10 pages.
Exhibit PMH-21—Documentation regarding Starmix Racun/Rumpai Herbicide (Date Unknown), 3 pages.
Exhibit PMH-22—article entitled Control of Eucalyptus grandis cut stumps by Keith Little et al., ICFR Bulletin Series, No. 02/98 (1998), 19 pages.
Exhibit PMH-23—article entitled the killing of Eucalyptus grandis multiple-stem cut-stumps in the Karkloof Project by Keith Little et al., ICFR Bulletin Series, No. Mar. 2000, 8 pages.
Exhibit PMH-24—Site Management and Productivity in Tropical Plantation Forests: A Progress Report (bears the date of Dec. 1999), 15 pages.
Exhibit PMH-25—article entitled Evaluation of herbicides for control of summer-growing weeds on fallows n south-eastern Australia, Australian Journal of Experimental Agriculture, vol. 30, (1990) 15 pages.
Exhibit PMH-26—article entitled Interaction between glyphosate and fluroxypyr improve mallow control, Crop Protection, vol. 21 (2002) by R. Chorbadjian, 5 pages.
Exhibit PMH-27—WO 2004/093546 (AU 2004232335 B2), Nov. 4, 2004, Applicant Monsanto Technology LLC, 108 pages.
Exhibit PMH-28—GB 2 267 825, Applicant DowElanco, date of publication Dec. 22, 1993, 29 pages.
Exhibit PMH-29—US 5703015 issued Dec. 30, 1997 (inventors Paul D. Berger et al.), 15 pages.

(Continued)

Primary Examiner — Janet Epps-Smith
Assistant Examiner — Courtney Brown
(74) Attorney, Agent, or Firm — Senniger Powers LLP; Joseph A. Schaper

(57) ABSTRACT

The present invention is directed to herbicidal compositions or formulations, and to methods of using such compositions or formulations to kill, or control the growth and proliferation of, unwanted plants. In particular, the present invention is directed to herbicidal compositions or formulations, as well as their methods of use, which comprise N-phosphonomethylglycine or a herbicidal derivative thereof, a pyridine analog or a herbicidal derivative thereof, and optionally one or more suitable surfactants, with N-phosphonomethylglycine being in excess relative to the pyridine analog. Such compositions cause early visual symptoms of treatment and/or enhanced effectiveness or control when applied to the foliage of plants.

26 Claims, No Drawings

(56) References Cited

OTHER PUBLICATIONS

Exhibit PMH-30—article by R.K. Howell et al. entitled Low Volume Foliar Applications of Triclopyr, Picloram, Imzazpyr and Glyphosate Mixtures for Rights-of-Way Cleanup, 1998 Proceedings, Southern Weed Science Society (1998) 4 pages.
Exhibit PMH-31—article by Galen M. Wright et al. entitled Understory Vegetation Control to Establish Oak Regeneration, North Central Weed Control Conference Proceedings, Columbus, Ohio, vol. 38 (1983) 2 pages.
Exhibit PMH-32—article by M.L. McCormack et al. entitled Timing Triclopyr and Glyphosate Treatments on Forest Brush, Northeastern Weed Sci. Soc., New York, NY, vol. 36 (1982) 7 pages.
Exhibit SG-1—Letter dated Oct. 20, 2011 from Monash University to IP Organisers Pty Ltd, 2 pages.
Abdelghani, A.A., Assessment of the Exposure of Workers Applying Herbicide Mixtures (2, 4-D+Roundup, Garlon-3A+Roundup), Toxicity and Fate of These Mixtures in the Environment—Summary Report (1995), 70 pages.
Abdelghani, A.A. et al., Toxicity Evaluation of Single and Chemical Mixtures of Roundup, Garlon-3A, 2,4-D, and Syndets Surfactant to Channel Catfish (*Ictalurus punctatus*), Bluegill Sunfish (*Lepomis microchirus*), and Crawfish (*Procambarus* spp.) (1997) pp. 237-243.
Arif, Anwar et al., Lalang Grass Control with Low Spray Volume of Glyphosate Herbicide, Symposium in Weed Science (Biotrop special Publication) No. 24, pp. 317-324 (1986).
Arsenovic, M. et al., Brighton Crop Protection Conference—Weeds (1991), Weed Control on Railways in Yugoslavia, p. 1159.
Chee, Y.K. et al., Sheep Grazing Reduces Chemical Weed Control in Rubber, pp. 120-123 (Date Unknown).
Chorbadjian R. et al., Interaction between glyphosate and fluroxypyr improve mallow control, Crop Protection, vol. 21 (2002) pp. 689-692.
Daggett R. Howard et al., Long-Term Effects of Herbicide and Pre-commercial Thinning on Young Spruce-Fir Stands: The Austin Pond Study, Silviculture Research, Cooperative Forestry Research Unit Annual Report 2001-2002, University of Maine, pp. 29-31.
Harahap, Widjaya, The Study of Glyphosate and its Mixture in Controlling General Weeds in Rubber Planting Strips, Symposium in Weed Science, BIOTROP Spec. Publ. No. 24 (1986), pp. 349-357.
Holt, H.A. et al., Controlling Woody Plants with Wiping Application, 39th Annual Southern Weed Sci. Soc. Proceedings, Nashville, Tennessee (1986), p. 364.
Howell, R.K. et al., Low Volume Foliar Applications of Triclopyr, Picloram, Imazapyr and Glyphosate Mixtures for Rights-of-Way Cleanup, Proceedings Southern Weed Science Society, Birmingham, Alabama (1998), pp. 195-197.
Jackson, Nelroy E., Control of Brush and Chaparral Species with Glyphosate, 38th Annual California Weed Conference, Fresno, California (1986), pp. 221-223.
Kay, S.H. et al., Effects of Tank Mixing Triclopyr Amine and Glyphosate on Control of Alligatorweed, Proc. Southern Weed Science Society, Little Rock, Arkansas (1992), p. 291.
Label and Material Safety Data Sheet for Eclipse Glyphosate Tolerant Canola Herbicide Tank-Mix (2002) Dow AgroSciences, 12 pages.
Lawlor, Frances M. et al., Response of swallow-wort to herbicides (2001), Weed Science, vol. 50, No. 2, Abstract only, 1 page.
Lawrie, J. et al., Effects of herbicide mixtures and additives on *Rhododendron ponticum*, Weed Research, vol. 33, pp. 25-34 (1993).
Leys, A.R. et al., Evaluation of herbicides for control of summer-growing weeds on fallows in south-eastern Australia, Austr. J. Experim. Agricult. (1990) vol. 30, No. 2, pp. 271-278.
Little, Keith et al., Control of Eucalyptus grandis cut stumps, ICFR Bulletin Series No. Feb. 1998, 16 pages.
Little, Keith M. et al., First rotation Eucalyptus macarthurii cut stump control in KwaZulu-Natal, South Africa, South African Forestry Journal No. 207, pp. 15-20, Jul. 2006.
Little, Keith et al., The killing of Eucalyptus grandis multiple-stem cut-stumps in the Karkloof Project, ICFR Bulletin Series No. Mar. 2000, 6 pages.
McCormack, M.L. et al., Glyphosate and Triclopyr Mixtures to Control Forest Brush, Northeastern Weed Science Society (1981) vol. 35, p. 218.
McCormack M.L. et al., Timing Triclopyr and Glyphosate Treatments on Forest Brush, Northeastern Weed Sci. Soc. (1982) New York, NY, vol. 36, pp. 209-214.
McDonald, Philip M. et al., Response of Young Ponderosa Pines, Shrubs, and Grasses to Two Release Treatments, USDA Forest Service Res. Note PSW-RN-419-Web 1996, 8 pages.
Obenshain, Karen R. et al., Spatial Analysis of Herbicide Decay Rates in Louisiana, Environmental Monitoring and Assessment (1997) vol. 48, pp. 307-316.
Seifert John R. et al., Pre and Post Herbicide Applications on Hardwood Seedlings, Proc. North Central Weed Sci. Soc., vol. 47 (1992), p. 98.
Sparacino, A.C. et al., Le Controle Des Rubus spp. Presentes Sur Les Rives Des Canaux D'Irrigation et Des Rizieres, 45th International Symposium on Crop Protection, Gent, May 4, 1993, Part III, MFLRA3 58(a), p. 1018-1025.
Supplemental Labeling for Roundup PRO Herbicide by Monsanto, (1996) EPA Reg. No. 524-475, 2 pages.
Wait, Jim D. et al., Weed Control in Glyphosate Resistant Corn, Dept. of Agronomy, University of Missouri-Columbia, 2 pages (Date Unknown).
Wright, Galen M. et al., Understory Vegetation Control to Establish Oak Regeneration, North Central Weed Control Conference Proceedings, Columbus, Ohio, vol. 38, 1983, p. 139.
Wyrill, J.B. et al., Glyphosate Toxicity to Common Milkweed and Hemp Dogbane as Influenced by Surfactants, Weed Science, vol. 25, No. 3, pp. 275-287, May 1977.
Yeiser, J.L., June, July and August Applications of Glyphosate Tank Mixes for Site Preparation, Proceedings Southern Weed Sci. Soc. (1991) San Antonio, TX, pp. 250-255.
"Registered Pesticides 1992-1994" prepared by Pesticides Board Malaysia, 3 pages.
Crockett, Dinah, Grammatically Correct, Retrieved Feb. 27, 2012 from http://www.uhv.edu/ac/newsletters/writing/grammartip2006.08.29.htm, 2 pages.
International Search Report dated Aug. 24, 2004 relating to International Application No. PCT/US2004/012368, 7 pages.
Statement of Grounds and Particulars in the Opposition of Australian Patent Application No. 2004232335 dated Jun. 23, 2011, 12 pages.
Exhibit PMH-1—Resume of Phillip Maxwell Hay (Oct. 2011), 4 pages.
Exhibit PMH-2—Federal Court of Australia, Practice Note CM 7, Expert Witnesses in Proceedings in the Federal Court of Australia (Oct. 2011), 3 pages.
Exhibit PMH-3—Glyphosate: A Unique Global Herbicide by John E. Franz, (p. 192) (1997), 4 pages.
Exhibit PMH-4—Glyphosate: A Unique Global Herbicide by John E. Franz (pp. 187-193) (1997), 36 pages.
Exhibit PMH-5—Documentation regarding Roundup CT Herbicide by Monsanto, NRA Approval No. 31394/1102, (Jun. 2002) 16 pages.
Exhibit PMH-6—Documentation regarding Roundup PowerMax Herbicide by Monsanto (bears the date of Nov. 2002), 14 pages.
Exhibit PMH-7—Documentation regarding Roundup Max Group M Herbicide by Monsanto (Date Unknown), 20 pages.
Exhibit PMH-8—WO 01/89302 published on Nov. 29, 2001 (Applicant: Monsanto Technology, LLC), 367 pages.
Exhibit PMH-9—article entitled Glyphosate Toxicity to Common Milkweed and Hemp Dogband as Influenced by Surfactants by J.B. Wyrill, Weed Science, vol. 25, Issue 3 (May 1977), 14 pages.
Exhibit PMH-10—Product Guide Book 2000, Dow AgroSciences (2000), 44 pages.
Exhibit PMH-11—Documentation on Nufarm Invader 600 Herbicide regarding Directions for Use (bears the date of Feb. 11, 2000), 5 pages.
Exhibit PMH-12—Documentation on Generex Triclopyr 600 Herbicide (bears the date of Jun. 14, 2000), 17 pages.
Exhibit PMH-13—Documentation on Garlon 4 Specialty Herbicide (bears the date of Sep. 8, 1995), 16 pages.
Exhibit PMH-14—Documentation on Garlon 3A, EPA Reg. No. 62719-37 (bears the year 1996), 16 pages.

(56) References Cited

OTHER PUBLICATIONS

Exhibit PMH-15—Documentation on Roundup CT Broadacre Herbicide (Mar. 31, 2000), 8 pages.

Exhibit PMH-16—Material Safety Data Sheet for Scotts Australia Pty. Ltd. (bears the date of Apr. 15, 2004), 5 pages.

Vermeulen, J.D., et al., A Guide to the Use of Herbicides, 1993, 14th Ed., pp. 112-123.

Milne, B., 1987 Results, Weed Research & Demonstration Unit, Agricultural Research & Veterinary Centre, Department of Agriculture, New South Wales, 4 pages.

The Herbicide Glyphosate, 1985, Grossbard and Atkinson, Eds., Butterworth & Co. (Publishers) Ltd., p. 223.

Chambers, A., "Field Crop Herbicide Guide 1997-1998", Institute for Integrated Agricultural Development, RMB 1145, Rutherglen, 3685, Kondinin Group, Publisher, pp. 337-338.

Milne, B., 1990 Results, Weed Research & Demonstration Unit, Agricultural Research & Veterinary Centre, NSW Agriculture & Fisheries, 3 pages.

Milne, B., 1992 Results, Weed Research & Demonstration Unit, Agricultural Research & Veterinary Centre, NSW Agriculture, 11 pages.

Roundup CT Broadacre Herbicide, Pubic Chemical Registration Information System, http://services.apvma.gov .au!Pubcris WebClientldetails.do?view=summary&pcode=316 . . . , downloaded Jun. 20, 2013, 6 pages.

Lontrel Herbicide Product Label, N.R.A. Label No. 31635/1102, approved Nov. 14, 2002, 12 pages.

Statutory Declaration of Phillip Maxwell Hay, filed Jun. 25, 2013 in Australian Patent Application No. 2004232335, 35 pages.

* cited by examiner

HERBICIDAL COMPOSITIONS CONTAINING GLYPHOSATE AND A PYRIDINE ANALOG

REFERENCE TO RELATED APPLICATIONS

This application is a continuation of U.S. application Ser. No. 10/829,572 (filed on Apr. 22, 2004), and claims priority from U.S. Provisional Application Ser. No. 60/496,031 (filed on Apr. 22, 2003), and U.S. Provisional Patent Application Ser. No. 60/552,065 (filed Mar. 10, 2004), the entire contents of which are incorporated herein by reference.

BACKGROUND OF THE INVENTION

The present invention relates generally to herbicidal compositions or formulations, and to methods of using such compositions to kill, or control the growth and proliferation of, unwanted plants. In particular, the present invention relates to herbicidal compositions, as well as their methods of use, which comprise N-phosphonomethylglycine, or a herbicidal derivative thereof, and a pyridine analog, or a herbicidal derivative thereof, optionally with one or more suitable surfactants. Such compositions cause early visual symptoms of treatment and/or enhanced effectiveness or control when applied to the foliage of plants.

Herbicidal compositions comprising the herbicide N-phosphonomethylglycine or derivatives thereof ("glyphosate"), are useful for suppressing the growth of, or killing, unwanted plants such as grasses, weeds and the like. Glyphosate typically is applied to the foliage of the target plant. After application the glyphosate is absorbed by the foliar tissue of the plant and translocated throughout the plant. Glyphosate noncompetitively blocks an important biochemical pathway which is common to virtually all plants, but which is absent in animals. Although glyphosate is very effective in killing or controlling the growth of unwanted plants, the uptake (i.e., absorption) of glyphosate by the plant foliar tissue and translocation of glyphosate throughout the plant is relatively slow. Visual symptoms that a plant has been treated with glyphosate may not appear until one week or more after treatment.

Compositions comprising glyphosate may be formulated with one or more surfactants to enhance their effectiveness for foliar application. When water is added to a composition formulated with surfactants, the resulting sprayable composition more easily and effectively covers the foliage (e.g., the leaves or other photosynthesizing organs) of plants. Glyphosate salts, for example, have been formulated with surfactants such as polyoxyalkylene-type surfactants including, among other surfactants, polyoxyalkylene alkylamines. Commercial formulations of glyphosate herbicide marketed under the trademark ROUNDUP® have been formulated by Monsanto with such a polyoxyalkylene alkylamine, in particular a polyoxyethylene tallowamine.

As a result of the somewhat slow development of visual symptoms that may result when glyphosate is utilized alone, formulations or compositions containing glyphosate and another herbicide have been suggested, in an attempt to achieve both early visual symptoms of plant treatment and prolonged control of the plant. For example, some have suggested using a tank mix composition containing glyphosate and a contact herbicide, such as a pyridine analog like triclopyr (i.e., [(3,5,6-trichloro-2-pyridinyl)oxy]acetic acid) or a herbicidal derivative thereof. However, to-date, such tank mixes have generally (i) employed relatively low weight ratios of glyphosate to, for example, triclopyr (wherein glyphosate and triclopyr are present in equal amounts, glyphosate is in a slight excess, or triclopyr is in excess), and/or (ii) not utilized a surfactant therein.

For example, R. K. Howell et al. (Southern Weed Science Society Proceedings, 195-197 (1998)) disclose the preparation of a tank mixture containing a surfactant TL90, Roundup Pro® and Garlon™ 4, the glyphosate (in Roundup Pro®) and triclopyr (in Garlon™ 4) being present in an apparent weight ratio of approximately 1.3:1, respectively.

G. M. Wright et al. (North Central Weed Control Conference Proceedings, vol. 38, 139 (1983)) disclose the preparation of a tank mixture of glyphosate and triclopyr in the apparent absence of a surfactant, the glyphosate and triclopyr, respectively, being present in an apparent weight ratio of approximately 1.5:1.

M. L. McCormack et al. (Northeastern Weed Society Proceedings, vol. 36, 209-214 (1982)) disclose the preparation of a tank mixture of glyphosate and triclopyr in the apparent absence of a surfactant, the glyphosate and triclopyr, respectively, being present in an apparent weight ratio of approximately 1.4:1.

J. Lawrie et al. (Weed Research, vol. 33, 25-34, (1993) appear to disclose the preparation of a tank mixture of glyphosate, triclopyr and a surfactant-containing mixture, wherein the glyphosate and triclopyr, respectively, appear to be present in a weight ratio of approximately 1.67:1.

W. Harahap et al. (Biotrop Special Publication, no. 24, 317-24 (1986)) disclose the preparation of tank mixtures of glyphosate and triclopyr or picloram, in the apparent absence of a surfactant. In the tank mixtures, glyphosate and triclopyr are, respectively, present in an apparent weight ratio of approximately 9.5:1 or 11.5:1, while glyphosate and picloram are present in an apparent weight ratio of approximately 7.7:1.

S. H. Kay et al. (Southern Weed Science Society Proceedings, 291 (1992)) disclose the preparation of a tank mixture of glyphosate and triclopyr in the apparent absence of a surfactant, the glyphosate and triclopyr, respectively, being present in a weight ratio of approximately 1:1.

A Roundup Pro® Supplemental Label (for application in California using a helicopter, EPA Reg. No. 524-475, Monsanto Company (1996)), discloses the optional preparation of a tank mixture of Roundup Pro® and Garlon™ 4 in varying weight ratios of glyphosate and triclopyr, respectively, as well as varying concentrations related thereto.

Tank mixtures require the user to purchase and store each herbicide used in the mixture separately, until the actual preparation of such mixtures in the field. The user must also measure out varying amounts of each herbicide used in the mixture. Therefore, a pre-packaged mixture (i.e., a concentrate) which already contains the desired herbicides in a single container may be desirable in some instances. However, concentrates may be difficult to prepare, for example when one of the herbicides is not soluble or miscible with the same desired solvent (e.g., water).

The solubility or miscibility problems sometimes encountered with concentrates may be overcome by preparing a concentrated emulsion formulation. A concentrated emulsion formulation consists of two phases and is a dispersion of one immiscible liquid (i.e., the discontinuous phase) in a second liquid (i.e., the continuous phase). If the continuous phase is water, the emulsion is an oil-in-water type emulsion and the water-immiscible liquid or solution may be referred to as the "oil" phase (regardless of its composition). In a concentrated emulsion formulation, the active ingredient may be dissolved in an organic solvent along with added emulsifiers and/or dispersants. When the concentrate is added to water, the active ingredient becomes dispersed throughout the water.

Such a concentrate, in the form of a microemulsion, was prepared in U.K. Patent Application No. GB 2 267 825 A, using a slight excess of the isopropylamine salt of glyphosate relative to the butoxyethyl ester of triclopyr (weight ratio of glyphosate to triclopyr approximately 1.6:1), and a high load or amount of triclopyr and two ethoxylated cocoamine surfactants, Ethomeen™ C-15 and C-25 (approximately 100 g/L triclopyr and approximately 285 g/L total surfactant).

SUMMARY OF THE INVENTION

Briefly, therefore, the present invention is directed to an aqueous herbicidal liquid concentrate, which may be diluted with water to provide an aqueous herbicidal application mixture for application to the foliage of a plant. The concentrate comprises glyphosate, or a herbicidal derivative thereof, in a concentration of at least about 50 grams acid equivalent per liter, a pyridine analog selected from the group consisting of triclopyr, clopyralid, dithiopyr, thiazopyr and picloram, or a herbicidal derivative thereof, and at least one surfactant, wherein (i) the glyphosate (acid equivalent basis) and the pyridine analog (acid equivalent basis) are present in a weight ratio of at least 1.7:1, and (ii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is further directed to an aqueous herbicidal liquid concentrate, which may be diluted with water to provide an aqueous herbicidal application mixture for application to the foliage of a plant. The concentrate comprises glyphosate, or a herbicidal derivative thereof, in a concentration of at least about 50 grams acid equivalent per liter, a pyridine analog selected from the group consisting of triclopyr, clopyralid, dithiopyr, thiazopyr and picloram, or a herbicidal derivative thereof, and at least one surfactant, wherein (i) the glyphosate (acid equivalent basis) and the pyridine analog (acid equivalent basis) are present in a weight ratio ranging from at least 1.7:1 to less than about 32:1, and (ii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal liquid concentrate, which may be diluted with water to provide an aqueous herbicidal application mixture for application to the foliage of a plant. The concentrate comprises glyphosate, or a herbicidal derivative thereof, a pyridine analog selected from the group consisting of triclopyr, clopyralid, dithiopyr, thiazopyr and picloram, or a herbicidal derivative thereof, and at least one surfactant in a concentration ranging from about 1 grams to 283 grams per liter, wherein (i) the glyphosate (acid equivalent basis) and the pyridine analog (acid equivalent basis) are present in a weight ratio of at least 1:1, glyphosate being in excess, and (ii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal liquid concentrate, which may be diluted with water to provide an aqueous herbicidal application mixture for application to the foliage of a plant. The concentrate comprises glyphosate, or a herbicidal derivative thereof, a pyridine analog selected from the group consisting of triclopyr, clopyralid, dithiopyr, thiazopyr and picloram, or a herbicidal derivative thereof, in a concentration ranging from about 1 gram to 99 grams (acid equivalent basis) per liter, and at least one surfactant, wherein (i) the glyphosate (acid equivalent basis) and the pyridine analog (acid equivalent basis) are present in a weight ratio of at least 1:1, glyphosate being in excess, and (ii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal liquid concentrate, which may be diluted with water to provide an aqueous herbicidal application mixture for application to the foliage of a plant. The concentrate comprises glyphosate, or a herbicidal derivative thereof, a pyridine analog selected from the group consisting of triclopyr, clopyralid, dithiopyr, thiazopyr and picloram, or a herbicidal derivative thereof, and at least one surfactant, wherein (i) the glyphosate (acid equivalent basis) and the pyridine analog (acid equivalent basis) are present in a weight ratio of at least 1:1, (ii) the glyphosate (acid equivalent basis) and the surfactant are present in a weight ratio of at least 1:1, wherein glyphosate is in excess in both instances, and (iii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal liquid concentrate, which may be diluted with water to provide an aqueous herbicidal application mixture for application to the foliage of a plant. The concentrate comprises glyphosate, or a herbicidal derivative thereof, and a pyridine analog selected from the group consisting of triclopyr, clopyralid, dithiopyr, thiazopyr and picloram, or a herbicidal derivative thereof, wherein the glyphosate (acid equivalent basis) and the pyridine analog (acid equivalent basis) are present in a weight ratio of at least 1:1, glyphosate being in excess, and further wherein (i) the pyridine analog or a herbicidal derivative thereof is present at a concentration of not greater than 99 grams (acid equivalent) per liter, and (ii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal liquid concentrate, which may be diluted with water to provide an aqueous herbicidal application mixture for application to the foliage of a plant. The concentrate comprises glyphosate, or a herbicidal derivative thereof, and a pyridine analog, or a herbicidal derivative thereof, wherein the glyphosate (acid equivalent basis) and the pyridine analog (acid equivalent basis) are present in a weight ratio of at least 1:1, glyphosate being in excess, and further wherein (i) the glyphosate (acid equivalent basis) or herbicidal derivative thereof is present at a concentration of not greater than 165 grams (acid equivalent) per liter, and (ii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal liquid concentrate which may be diluted with water to provide an aqueous herbicidal application mixture for application to the foliage of a plant. The concentrate comprises at least one glyphosate salt predominantly in the form of potassium glyphosate, monoethanolamine glyphosate, or a mixture thereof; a pyridine analog selected from the group consisting of triclopyr, clopyralid, fluoroxypyr, dithiopyr, thiazopyr and picloram, or a herbicidal derivative thereof; and, at least one surfactant in a concentration less than 20 grams per liter; wherein the glyphosate (acid equivalent basis) and the pyridine analog (acid equivalent basis) are present in a weight ratio of at least 1:1, glyphosate being in excess.

The present invention is further directed to an aqueous herbicidal liquid concentrate, which may be diluted with water to provide an aqueous herbicidal application mixture for application to the foliage of a plant. The concentrate comprises glyphosate, or a herbicidal derivative thereof, in a concentration of less than 65 grams acid equivalent per liter, picloram, or a herbicidal derivative thereof, and at least one surfactant, wherein (i) the glyphosate (acid equivalent basis) and the picloram (acid equivalent basis) are present in a weight ratio of at least 1:1, with glyphosate being in excess. Optionally, when the glyphosate is predominantly in the form of a salt, said salt may be selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to a method of killing or controlling weeds or unwanted vegetation. The method comprises diluting one of the preceding liquid concentrates in a convenient amount of water to form an application mixture, and then applying a herbicidally effective amount of the application mixture to the foliage of the weeds or unwanted vegetation.

The present invention is still further directed to an aqueous herbicidal composition useful for killing or controlling the growth of unwanted plants. The composition comprises glyphosate, or a herbicidal derivative thereof, a pyridine analog, or a herbicidal derivative thereof, and at least one surfactant, wherein (i) the glyphosate (acid equivalent basis) and the pyridine analog (acid equivalent basis) are present in a weight ratio of at least 7.6:1, and (ii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal composition useful for killing or controlling the growth of unwanted plants. The composition comprises glyphosate, or a herbicidal derivative thereof, a pyridine analog selected from the group consisting of triclopyr, clopyralid, dithiopyr, thiazopyr and picloram, or a herbicidal derivative thereof, in a concentration of not greater than 3.9 grams (acid equivalent basis) per liter, and at least one surfactant, wherein (i) the glyphosate (acid equivalent basis) and the pyridine analog (acid equivalent basis) are present in a weight ratio of at least about 1:1, glyphosate being in excess, and (ii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal composition useful for killing or controlling the growth of unwanted plants. The composition comprises glyphosate, or a herbicidal derivative thereof, a pyridine analog selected from the group consisting of triclopyr, clopyralid, dithiopyr, thiazopyr and picloram, or a herbicidal derivative thereof, and at least one surfactant, wherein (i) the surfactant concentration is not greater than 3.9 grams per liter, (ii) glyphosate (acid equivalent basis) and the pyridine analog (acid equivalent basis) are present in a weight ratio of at least 3:1, and (iii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal composition useful for killing or controlling the growth of unwanted plants. The composition comprises glyphosate, or a herbicidal derivative thereof, a pyridine analog, or a herbicidal derivative thereof, and at least one surfactant, wherein (i) the surfactant concentration is not greater than 6.6 grams per liter, (ii) glyphosate (acid equivalent basis) and the pyridine analog (acid equivalent basis) are present in a weight ratio of at least 5:1, and (iii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal composition useful for killing or controlling the growth of unwanted plants. The composition comprises glyphosate, or a herbicidal derivative thereof, a pyridine analog, or a herbicidal derivative thereof, and at least one surfactant, wherein (i) the surfactant concentration is not greater than 9.3 grams per liter, (ii) glyphosate (acid equivalent basis) and the pyridine analog (acid equivalent basis) are present in a weight ratio of at least 7:1, and (iii) when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal composition useful for killing or controlling the growth of unwanted plants. The composition comprises glyphosate or a herbicidal derivative thereof, a pyridine analog or a herbicidal derivative thereof, and at least one surfactant, wherein either (i) the glyphosate concentration (acid equivalent basis) is not greater than 16.2 grams per liter, and glyphosate (acid equivalent basis) and the pyridine analog (acid equivalent basis) are present in a weight ratio of at least 4:1, or (ii) the glyphosate concentration (acid equivalent basis) is not greater than 23.8 grams per liter, and glyphosate (acid equivalent basis) and the pyridine analog (acid equivalent basis) are present in a weight ratio of at least 6:1, and further when the glyphosate is predominantly in the form of a salt, said salt is selected from the group consisting of a sodium salt, an ammonium salt, an alkylammonium salt, a $C_{3-16}$ alkanolammonium salt, a di-ammonium salt, an alkylamine salt, a $C_{3-16}$ alkanolamine salt, an alkylsulfonium salt, a sulfoxonium salt, and combinations thereof.

The present invention is still further directed to an aqueous herbicidal composition useful for killing or controlling the growth of unwanted plants. The concentrate comprises at least one glyphosate salt predominantly in the form of potassium glyphosate, monoethanolamine glyphosate, or a mixture thereof; and a pyridine analog selected from the group consisting of triclopyr, clopyralid, fluoroxypyr, dithiopyr, thiazopyr and picloram, or a herbicidal derivative thereof; wherein (i) the glyphosate salt is present in a concentration less than 180 grams acid equivalent per liter and the glyphosate salt (acid equivalent basis) and the pyridine analog (acid equivalent basis) are present in a weight ratio of at least 1:1, glyphosate being in excess; (ii) the glyphosate salt is present in a concentration less than 240 grams acid equivalent per liter and the glyphosate salt (acid equivalent basis) and the pyridine analog (acid equivalent basis) are present in a weight ratio of at least 2:1; (iii) the glyphosate salt is present in a concentration less than 270 grams acid equivalent per liter and the glyphosate salt (acid equivalent basis) and the pyridine analog (acid equivalent basis) are present in a weight ratio of at least 3:1; (iv) the glyphosate salt is present in a concentration less than 288 grams acid equivalent per liter and the glyphosate salt (acid equivalent basis) and the pyridine analog (acid equivalent basis) are present in a weight ratio of at least 4:1; (v) the glyphosate salt is present in a concentration less than 300 grams acid equivalent per liter and the glyphosate salt (acid equivalent basis) and the pyridine analog (acid equivalent basis) are present in a weight ratio of at least 5:1; (vi) the glyphosate salt is present in a concentration less than 308 grams acid equivalent per liter and the glyphosate salt (acid equivalent basis) and the pyridine analog (acid equivalent basis) are present in a weight ratio of at least 6:1; (vii) the glyphosate salt is present in a concentration less than 315 grams acid equivalent per liter and the glyphosate salt (acid equivalent basis) and the pyridine analog (acid equivalent basis) are present in a weight ratio of at least 7:1; (viii) the glyphosate salt is present in a concentration less than 320 grams acid equivalent per liter and the glyphosate salt (acid equivalent basis) and the pyridine analog (acid equivalent basis) are present in a weight ratio of at least 8:1; (ix) the glyphosate salt is present in a concentration less than 324 grams acid equivalent per liter and the glyphosate salt (acid equivalent basis) and the pyridine analog (acid equivalent basis) are present in a weight ratio of at least 9:1; or (x) the glyphosate salt is present in a concentration less than 326 grams acid equivalent per liter and the glyphosate salt (acid equivalent basis) and the pyridine analog (acid equivalent basis) are present in a weight ratio of at least 10:1.

The present invention is still further directed to a method for killing or controlling the growth of unwanted plants. The method comprises contacting the foliage of said plants with a herbicidally effective amount of one of the previously described aqueous herbicidal compositions.

The present invention is still further directed to a herbicidal particulate solid concentrate which may be dissolved or dispersed in water to provide an aqueous herbicidal application mixture for application to the foliage of a plant. The solid concentrate comprises glyphosate, or a herbicidal derivative thereof, and a pyridine analog, or a herbicidal derivative thereof, wherein a weight ratio (a.e. basis) of glyphosate to the pyridine analog is at least about 1:1, glyphosate being in excess, and further wherein when the glyphosate is predominantly in the form of a salt. Optionally, one or more surfactants may be present in the herbicidal particulate solid concentrate.

The present invention is still further directed to a method of killing or controlling weeds or unwanted vegetation. The method comprises diluting or dissolving the previously described solid particulate concentrate in a convenient amount of water to form an application mixture, and then applying a herbicidally effective amount of the application mixture to the foliage of the weeds or unwanted vegetation.

The present invention is still further directed to one or more of the previously noted methods for killing or controlling the growth of unwanted plants which comprises contacting the foliage of said plants with such an aqueous herbicidal composition, wherein said herbicidal composition is brought into contact with, or applied to, said foliage using means other than a helicopter.

The present invention is still further directed to a method of killing or controlling weeds or unwanted plants. The method comprises diluting an aqueous herbicidal concentrate composition in an amount of water to form an application mixture; and, applying a herbicidally effective amount of the application mixture to foliage of the weeds or unwanted plants, wherein the weeds or unwanted plants comprise poison ivy, poison oak, kudzu, multiflora rose, golden rod, blue fescue, red maple, and/or red oak, and the aqueous herbicidal concentrate composition comprises glyphosate or a herbicidal derivative thereof; a pyridine analog selected from the group consisting of triclopyr, clopyralid, dithiopyr, thiazopyr and picloram, or a herbicidal derivative thereof; and, at least one surfactant.

The present invention is still further directed to one or more of the previously described aqueous herbicidal liquid concentrates, aqueous herbicidal compositions, herbicidal particulate solid concentrates, and methods for the use thereof, wherein said pyridine analog is triclopyr, a derivative thereof, or some combination which includes triclopyr.

The present invention is still further directed to one or more of the previously described aqueous herbicidal liquid concentrates, aqueous herbicidal compositions, herbicidal particulate solid concentrates, and methods for the use thereof, wherein said pyridine analog is clopyralid, a derivative thereof, or some combination which includes clopyralid.

The present invention is still further directed to one or more of the previously described aqueous herbicidal liquid concentrates, aqueous herbicidal compositions, herbicidal particulate solid concentrates, and methods for the use thereof, wherein said pyridine analog is dithiopyr, a derivative thereof, or some combination which includes dithiopyr.

The present invention is still further directed to one or more of the previously described aqueous herbicidal liquid concentrates, aqueous herbicidal compositions, herbicidal particulate solid concentrates, and methods for the use thereof, wherein said pyridine analog is thiazopyr, a derivative thereof, or some combination which includes thiazopyr.

The present invention is still further directed, where appropriate, to one or more of the previously described aqueous herbicidal liquid concentrates, aqueous herbicidal compositions, herbicidal particulate solid concentrates, and methods for the use thereof, wherein said pyridine analog is picloram, a derivative thereof, or some combination which includes picloram.

The present invention is still further directed, where appropriate, to one or more of the previously described aqueous herbicidal liquid concentrates, aqueous herbicidal compositions, herbicidal particulate solid concentrates, and methods for the use thereof, wherein said pyridine analog is fluoroxypyr, a derivative thereof, or some combination which includes fluoroxypyr.

The present invention is still further directed, where appropriate, to one or more of the previously described aqueous herbicidal liquid concentrates, aqueous herbicidal compositions, herbicidal particulate solid concentrates, and methods for the use thereof, wherein said pyridine analog is a combination or mixture of one or more of triclopyr, fluoroxypyr, dithiopyr, thiazopyr, picloram, or derivatives thereof.

The present invention is still further directed, where appropriate, to one or more of the previously described aqueous herbicidal liquid concentrates, aqueous herbicidal compositions, herbicidal particulate solid concentrates, and methods for the use thereof, wherein said pyridine analog is a combination or mixture of triclopyr and clopyralid, or derivatives thereof.

The present invention is still further directed, where appropriate, to one or more of the previously described aqueous herbicidal liquid concentrates, aqueous herbicidal compositions, herbicidal particulate solid concentrates, and methods for the use thereof, wherein said pyridine analog is a combination or mixture of one or more of triclopyr, clopyralid, fluoroxypyr, or derivatives thereof.

DETAILED DESCRIPTION OF THE INVENTION

According to the present invention, coherbicidal compositions or formulations containing glyphosate or a derivative thereof, a pyridine analog (e.g., triclopyr, clopyralid, fluoroxypyr, dithiopyr, thiazopyr, picloram, etc., or a combination thereof) or a derivative thereof, and optionally a suitable surfactant, are provided that are advantageous for a number of reasons, including rapid uptake by the target plant, early visual symptoms of plant treatment, and control of a broad spectrum of plant species, as well as enhanced, more consistent control of unwanted plants. Accordingly, in at least some embodiments, lower application rates may potentially be used for the pyridine analog and/or the surfactant(s) applied, without a loss of effectiveness of plant control.

I. GLYPHOSATE AND PYRIDINE ANALOG COHERBICIDES

A. Coherbicide Combinations and Forms

The compositions or formulations of the present invention comprise at least two herbicides, and optionally at least one surfactant. A first component of the compositions of the present invention may be, for example, N-phosphonomethylglycine ("glyphosate"), a salt or adduct thereof, or a compound which is converted to glyphosate in plant tissues or which otherwise provides glyphosate ion. In this regard it is to be noted that the term "glyphosate," when used herein, is to be understood to encompass such derivatives unless the context requires otherwise.

Glyphosate salts that can be used according to this invention include but are not restricted to, for example, alkali metal salts, for example sodium and potassium salts, ammonium salts, alkylammonium salts (e.g., $C_{1-16}$ alkylammonium, or alternatively $C_{3-16}$ alkylammonium), alkanolammonium salts (e.g., $C_{1-16}$ alkanolammonium, or alternatively $C_{3-16}$ alkanolammonium), di-ammonium salts such as dimethylammonium, alkylamine salts, for example dimethylamine and isopropylamine salts, alkanolamine salts (e.g., $C_{1-16}$ alkanolamine, or alternatively $C_{3-16}$ alkanolamine), for example ethanolamine salts, alkylsulfonium salts (e.g., $C_{1-16}$ alkylsulfonium, for example trimethylsulfonium salts), sulfoxonium salts, and mixtures or combinations thereof. For some preferred embodiments, preferred glyphosate salts include for example the potassium salt, isopropylamine salt, ammonium salt, di-ammonium salt, sodium salt, monoethanolamine salt, and trimethylsulfonium salt, as well as combinations thereof. For still other preferred embodiments, glyphosate is predominantly in the form of a salt other than a potassium salt or a monoethanolamine or monoethanolammonium salt; that is, in an alternative preferred embodiment glyphosate is a salt predominantly in the form of the isopropylamine salt, the ammonium salt, the di-ammonium salt, the sodium salt, the trimethylsulfonium salt, or some combination thereof.

The herbicidal properties of N-phosphonomethylglycine and its derivatives were first discovered by Franz, then disclosed and patented in U.S. Pat. No. 3,799,758, issued Mar. 26, 1974. A number of herbicidal salts of N-phosphonomethylglycine were patented by Franz in U.S. Pat. No. 4,405,531, issued Sep. 20, 1983. The disclosures of both of these patents are hereby incorporated by reference.

Various salts of N-phosphonomethylglycine are commercially significant, in part because they are water soluble. Many of the salts listed herein are highly water soluble, thereby allowing for highly concentrated solutions that can be diluted at the site of use. In accordance with the methods of this invention, as they pertain to glyphosate herbicide, a solution containing a herbicidally effective amount of glyphosate, and other components as described elsewhere herein (e.g., a pyridine analog, and optionally a surfactant), is applied to the foliage of plants.

A pyridine analog or derivative thereof (i.e., an acid, a salt or an ester form thereof), such as one or more of those disclosed in U.S. Pat. No. 4,692,184 (which is incorporated in its entirety herein by reference for all relevant purposes), is another component of the composition of the present invention. In this regard it is to be noted that the phrase "pyridine analogs", as well as variations thereof, is intended to generally refer to a class of herbicides that includes, for example: triclopyr (i.e., [(3,5,6-trichloro-2-pyridinyl)oxy]acetic acid), clopyralid (i.e., 3,6-dichloro-2-pyridine carboxylic acid), fluoroxypyr (i.e., [(4-amino-3,5-dichloro-6-fluoro-pyridyl)oxy] acetic acid), dithiopyr (i.e., S,S-dimethylester-2-(difluoromethyl)-4-(2-methylpropyl)-6-(trifluoromethyl)-3,5-pyridine dicarbothioic acid), thiazopyr (i.e., methyl 2-(difluoromethyl)-5-(4,5-dihydro-2-thiazolyl)-4-(2-methylpropyl)-6-(trifluoromethyl)-3-pyridine carboxylate), and picloram (i.e., 4-amino-3,5,6-trichloropicolinic acid), as well as derivatives thereof, in all of their various forms, including for example the acid, the salt (e.g., amine salt, such as monoethanolamine or triethylamine), and the ester (e.g., butoxyethyl ester). Such compounds may be characterized, in one aspect of the present invention, by the rapid symptomology and more consistent control they impart.

In this regard it is to be noted that the present invention encompasses essentially any formulation disclosed herein (e.g., concentrate, solid or tank mix) which comprises glyphosate and any one of triclopyr, clopyralid, fluoroxypyr, dithiopyr, thiazopyr, picloram, or a derivative thereof, as well as any combination or mixture which includes any one, two, there, four, five or six of these pyridine analogs. Exemplary co-herbicidal combinations are set forth in greater detail in Coherbicide Tables A-E, below (which illustrate that glyphosate, or one of its salts, can be combined with pyridine analog herbicides to form a herbicidal composition comprising two to seven actives, wherein: G=glyphosate; Tr=triclopyr; C=clopyralid; F=fluoroxypyr; D=dithiopyr; Th=thiazopyr; P=picloram; and "Active No." is a herbicide combination reference number):

TABLE A

Glyphosate in combination with one pyridine analog herbicide

| Active No. | Herbicides |
|---|---|
| 1 | G + Tr |
| 2 | G + C |
| 3 | G + F |
| 4 | G + D |
| 5 | G + Th |
| 6 | G + P |

TABLE B

Glyphosate in combination with two pyridine analog herbicides

| Active No. | Herbicides |
|---|---|
| 7 | G + Tr + P |
| 8 | G + Tr + C |
| 9 | G + Tr + D |
| 10 | G + Tr + Th |
| 11 | G + Tr + F |
| 12 | G + P + C |
| 13 | G + P + D |
| 14 | G + P + Th |
| 15 | G + P + F |
| 16 | G + C + D |
| 17 | G + C + Th |
| 18 | G + C + F |
| 19 | G + D + Th |
| 20 | G + D + F |
| 21 | G + Th + F |

TABLE C

Glyphosate in combination with three pyridine analog herbicides

| Active No. | Herbicides |
|---|---|
| 22 | G + Tr + P + C |
| 23 | G + Tr + P + D |
| 24 | G + Tr + P + Th |
| 25 | G + Tr + P + F |
| 26 | G + Tr + C + D |
| 27 | G + Tr + C + Th |
| 28 | G + Tr + C + F |
| 29 | G + Tr + D + Th |
| 30 | G + Tr + D + F |
| 31 | G + Tr + Th + F |
| 32 | G + P + C + D |
| 33 | G + P + C + Th |
| 34 | G + P + C + F |
| 35 | G + P + D + Th |
| 36 | G + P + D + F |
| 37 | G + P + Th + F |
| 38 | G + C + D + Th |
| 39 | G + C + D + F |
| 40 | G + C + Th + F |
| 41 | G + D + Th + F |

TABLE D

Glyphosate in combination with four pyridine analog herbicides

| Active No. | Herbicides |
|---|---|
| 42 | G + Tr + P + C + D |
| 43 | G + Tr + P + C + Th |
| 44 | G + Tr + P + C + F |
| 45 | G + Tr + P + D + Th |
| 46 | G + Tr + P + D + F |
| 47 | G + Tr + P + Th + F |
| 48 | G + Tr + C + D + Th |
| 49 | G + Tr + C + D + F |
| 50 | G + Tr + C + Th + F |
| 51 | G + Tr + D + Th + F |
| 52 | G + P + C + D + Th |
| 53 | G + P + C + D + F |
| 54 | G + P + C + Th + F |
| 55 | G + P + D + Th + F |
| 56 | G + C + D + Th + F |

TABLE E

Glyphosate in combination with five pyridine analog herbicides

| Active No. | Herbicides |
|---|---|
| 57 | G + Tr + P + C + D + Th |
| 58 | G + Tr + P + C + D + F |
| 59 | G + Tr + P + C + Th + F |
| 60 | G + Tr + P + D + Th + F |
| 61 | G + Tr + C + D + Th + F |
| 62 | G + P + C + D + Th + F |

In one preferred embodiment, the pyridine analog is selected from the group consisting of triclopyr, clopyralid, dithiopyr, thiazopyr, picloram, or some combination thereof. In an alternative preferred embodiment, the pyridine analog is selected from the group consisting of triclopyr, clopyralid, dithiopyr, thiazopyr, or some combination thereof. In yet another preferred embodiment, the pyridine analog is selected from the group consisting of triclopyr, clopyralid, dithiopyr, or some combination thereof. In yet another preferred embodiment, the pyridine analog is selected from the group consisting of triclopyr, clopyralid, or a combination thereof. In yet another preferred embodiment, the pyridine analog is selected from the group consisting of triclopyr, dithiopyr, thiazopyr, or some combination thereof. In yet another preferred embodiment, the pyridine analog is selected from the group consisting of triclopyr, clopyralid, fluoroxypyr, or some combination thereof.

With respect to the ester and salt forms of the pyridine analogs or derivatives thereof of the present invention, it is to be noted that the present invention encompasses essentially any such ester or salt known to one of ordinary skill in the art, or which may be prepared thereby using techniques known in the art. Exemplary salts may include alkali metal salts, for example sodium and potassium salts, ammonium salts, alkylammonium salts (e.g., $C_{1-16}$ alkylammonium), alkanolammonium salts (e.g., $C_{1-16}$ alkanolammonium), di-ammonium salts such as dimethylammonium, alkylamine salts, for example dimethylamine and isopropylamine salts, alkanolamine salts, for example ethanolamine salts, alkylsulfonium salts (e.g., $C_{1-16}$ alkylsulfonium, for example trimethylsulfonium salts), sulfoxonium salts, and mixtures or combinations thereof.

B. Concentrations and Ratios

The relative amounts of glyphosate and the pyridine analog (e.g., triclopyr, clopyralid, fluoroxypyr, dithiopyr, thiazopyr, picloram, etc., or a combination thereof) present in a contemplated herbicidal composition (i.e., a particulate solid concentrate, or liquid concentrate, or alternatively a ready-to-use, or tank-mix, composition) may vary depending upon many factors, including for example the plant species to be controlled and the method of application. Generally speaking, however, the concentrations of these herbicides, and optionally a surfactant and/or some other additive (as described elsewhere herein), in the herbicidal compositions of the invention is sufficient to provide at least about 70% control (as determined by means known in the art) within about 50 days, preferably about 40 days, more preferably about 30 days, still more preferably about 20 days, still more preferably about 15 days, still more preferably about 10 days, still more preferably about 5 days, and even still more preferably about 1 day, or less, after application of the composition to a plant. In a more preferred embodiment, the concentration of these herbicides, and optionally a surfactant and/or some other additive, in the herbicidal compositions of the invention is sufficient to provide at least about 80%, more preferably at least about 85%, still more preferably at least about 90%, and still more preferably at least about 95%, control, or more, within about 50 days, preferably about 40 days, more preferably about 30 days, still more preferably about 20 days, still more preferably about 15 days, still more preferably about 10 days, still more preferably about 5 days, and even still more preferably about 1 day, or less, after application of the composition to a plant.

Additionally, the concentrations of these herbicides, and optionally a surfactant and/or some other additive (as described elsewhere herein), in the herbicidal compositions of the invention is sufficient to provide at least about 70% control of plant regrowth (as determined by means known in the art) for at least about 20, preferably at least about 30, more preferably at least about 40, still more preferably at least about 50, still more preferably at least about 60, still more preferably at least about 70, still more preferably at least about 80, or even still more preferably at least about 90, days after application of the composition to a plant. In a more preferred embodiment, the concentrations of these herbicides, and optionally a surfactant and/or some other additive, in the herbicidal compositions of the invention is sufficient to provide at least about 80%, more preferably at least about 85%, still more preferably at least about 90%, or still more preferably at least about 95% control, or more, for at least about 20, more preferably at least about 30, still more preferably at least about 40, still more preferably at least about 50, still more preferably at least about 60, still more preferably at least about 70, still more preferably at least about 80, or even still more preferably at least about 90, days after application to the plant.

Accordingly, in some embodiments of the present invention (e.g., the concentrate herbicidal composition), the glyphosate concentration may be at least about 50 grams, preferably at least about 75 grams, more preferably at least about 100 grams, still more preferably at least about 125 grams, still more preferably at least about 150 grams, still more preferably at least about 175 grams, still more preferably at least about 200 grams, still more preferably at least about 225 grams, still more preferably at least about 250 grams, (acid equivalent) per liter, or more (e.g., at least about 300 grams, at least about 350 grams, at least about 400 grams, at least about 450 grams, at least about 500 grams, at least 550 grams, at least 600 grams per liter, or more). The glyphosate concentration may therefore range from, for example, about 50 to about 500 grams (a.e.) per liter, from about 100 to about 400 grams per liter, from about 150 to about 300 grams per liter, or from about 175 to about 250 grams per liter.

In an alternative embodiment, the concentration of glyphosate may be no greater than 165 grams per liter (e.g., no greater than 160 grams per liter, 155 grams per liter, 150 grams per liter, 140 grams per liter, or even no greater than about 130, about 120, about 110, about 100, about 75 grams per liter or less). The glyphosate concentration may therefore range, for example, from about 100 to no greater than 160 grams per liter, or from about 110 to no greater than 150 grams per liter.

In still other embodiments (e.g., a ready-to-use composition, also known and referred to herein as a tank mix composition), the glyphosate concentration may be less than about 50, preferably less than about 45, more preferably less than about 40, still more preferably less than about 35, still more preferably less than about 30, or even still more preferably less than about 25 grams (a.e.) per liter (e.g., about 2, about 4, about 6, about 8, about 10, about 12, about 14, about 16, about 18 or about 20 grams (a.e.) per liter). Accordingly, the glyphosate concentration may range, for example, from about 2 to about 50 grams (a.e.) per liter, from about 4 to about 25, from about 6 to about 15, or from about 8 to about 12 grams (a.e.) per liter. In some instances, such as wherein:

(i) the weight ratio (a.e. to a.e.) of glyphosate to the pyridine analog is at least 4:1 (e.g., at least about 5:1, 6:1, 7:1, 8:1, 9:1, 10:1, 11:1, 12:1, 13:1, 14:1, 15:1, 20:1, 40:1, 60:1, 80:1, or even 100:1), the concentration of glyphosate may be no greater than 16.2 grams (a.e.) per liter (e.g., no greater than about 16, about 15.5, about 15, about 14.5, about 14, about 13.5, about 13, about 12.5, about 12, about 11.5, about 11, about 10.5, about 10, about 9.5, about 9, about 8.5, about 8, about 7.5, about 7, about 6.5, about 6, about 5.5, about 5, etc., the concentration thus ranging from, for example, about 5 to about 16, from about 7 to about 14, or from about 8 to about 12, grams (a.e.) per liter); exemplary combinations include a ratio of at least 4:1, about 8:1, or even about 10:1 with a glyphosate concentration of less than about 15 grams (a.e.) per liter, 12 grams (a.e.) per liter, 10 grams (a.e.) per liter, or even 8 grams (a.e.) per liter; and/or (ii) the weight ratio (a.e. to a.e.) of glyphosate to pyridine analog is at least 6:1 (e.g., at least about 7:1, 8:1, 9:1, 10:1, 11:1, 12:1, 13:1, 14:1, 15:1, 20:1, 40:1, 60:1, 80:1, or even 100:1), the concentration of glyphosate may be no greater than 23.8 grams (a.e.) per liter (e.g., no greater than about 23.5, about 23, about 22.5, about 22, about 21.5, about 21, about 20.5, about 20, about 19.5, about 19, about 18.5, about 18, about 17.5, about 17, about 16.5, about 16, about 15.5, about 15, about 14.5, about 14, about 13.5, about 13, about 12.5, about 12, about 11.5, about 11, about 10.5, about 10, about 9.5, about 9, about 8.5, about 8, about 7.5, about 7, about 6.5, about 6, about 5.5, about 5, etc., the concentration thus ranging from, for example, about 5 to about 22, from about 6 to about 20, or from about 8 to about 15, grams (a.e.) per liter); exemplary combinations include a ratio of at least 6:1, about 8:1, or even about 10:1 with a glyphosate concentration of less than about 20 grams (a.e.) per liter, 15 grams (a.e.) per liter, 12 grams (a.e.) per liter, 10 grams (a.e.) per liter, or even 8 grams (a.e.) per liter.

With respect to the glyphosate concentration, it is to be noted that as the concentration of glyphosate increases, the concentration of one or more other ingredients in the present composition may be reduced to maintain the solubility of one or more of the ingredients therein (i.e., to ensure these ingredients remain in solution).

The concentration of the pyridine analog in the herbicidal composition of the present invention may also vary. For example, the concentration may preferably be sufficient to provide visual symptoms of herbicide treatment within about 5 days, preferably about 4 days, or more preferably about 3 days after application of the composition to the plant, and in some instances may be sufficient to provide such symptoms within about 2 days, about 1 day or even less, after the application. However, in this regard it is to be noted that the concentration of the pyridine analog is also preferably controlled, such that it is not substantially antagonistic to the herbicidal activity of the glyphosate, or glyphosate derivative, within the composition.

Accordingly, in some embodiments of the present invention (e.g., the concentrate herbicidal composition), the concentration of the pyridine analog may be, for example, at least about 1, about 2, about 4, about 6, about 8, about 10, about 15, about 20, about 25, about 30, about 35, about 40, about 45, about 50, about 60, about 70, about 80, about 90, about 100 or more grams (a.e.) per liter. The concentration of the pyridine analog may therefore range, for example, from about 1 to about 99 or 100 grams (a.e.) per liter (e.g., about 1 to about 99 or 100, about 2 to about 80, about 4 to about 60, about 6 to about 40, or about 8 to about 20, grams (a.e.) per liter).

In these or other embodiments of the present invention, it is to be noted that the concentration may alternatively be not greater than 99 grams (a.e.) per liter (e.g., not greater than about 95, about 90, about 85, about 80, about 75, about 70, about 65, about 60, about 55, about 50, about 40, about 30, about 20, about 10, about 5 or less grams (a.e.) per liter). Accordingly, the concentration of the pyridine analog may range from, for example, about 1 to less than 99 grams (a.e.) per liter (e.g., from about 2 to less than about 80, from about 4 to less than about 60, from about 6 to less than about 40, or from about 8 to less than about 20, grams (a.e.) per liter).

In still other embodiments (e.g., a ready-to-use composition), the concentration of the pyridine analog may be less than about 25, about 15 or even about 10 grams (a.e.) liter, the concentration ranging for example from about 0.2 to about 10 grams (a.e.) per liter, from about 0.4 to about 6, from about 0.6 to about 4, or from about 0.8 to about 2 grams (a.e.) per liter. Additionally, or alternatively, the concentration of the pyridine analog may be not greater than 3.9 grams (a.e.) per liter (e.g., not greater than about 3.8, about 3.7, about 3.6, about 3.5, about 3.4, about 3.3, about 3.2, about 3.1, about 3, about 2.8, about 2.6, about 2.4, about 2.2, about 2, about 1.8, about 1.6, about 1.4, about 1.2, about 1, about 0.8, about 0.6, about 0.4, about 0.2 grams (a.e.) per liter or less, the concentration ranging for example from about 0.2 to about 3.5 grams (a.e.) per liter, from about 0.4 to about 3, from about 0.6 to about 2.5, or from about 0.8 to about 2 grams (a.e.) per liter).

With respect to the weight ratio (a.e. to a.e.) of glyphosate to the pyridine analog, generally speaking this is greater than about 1:1 (i.e., glyphosate is in excess); that is, this ratio may be at least about 1.1:1, about 1.2:1, about 1.3:1, about 1.4:1, about 1.5:1, about 1.6:1, about 1.7:1, about 1.8:1, about 1.9:1, about 2:1, about 2.2:1, about 2.4:1, about 2.6:1, about 2.8:1, about 3:1, about 4:1, about 5:1, about 6:1, about 7:1, about 8:1, about 9:1, about 10:1, about 11:1, about 12:1, about 13:1, about 14:1, about 15:1, about 20:1, about 25:1, about 30:1, about 35:1, about 40:1, about 45:1, about 50:1 or more (e.g., about 60:1, about 70:1, about 80:1, about 90:1 or even about 100:1). Accordingly, this ratio may range from about 1:1 to about 100:1, from about 2:1 to about 80:1, from about 4:1 to about 60:1, from about 6:1 to about 40:1, or from about 8:1 to about 20:1.

Alternatively, in some embodiments (e.g., a ready-to-use composition), this ratio may be at least 7.6:1, and preferably may be at least about 7.7:1, about 7.8:1, about 7.9:1, about 8:1, about 8.2:1, about 8.4:1, about 8.6:1, about 8.8:1, about 9:1, about 9.2:1, about 9.4:1, about 9.6:1, about 9.8:1, about 10:1 or more (e.g., about 11:1, about 12:1, about 13:1, about 14:1, about 15:1, about 20:1, about 25:1, about 30:1, about 35:1, about 40:1, about 45:1, about 50:1, about 60:1, about 70:1, about 80:1, about 90:1 or even about 100:1). Accordingly, this ratio ranges from, for example, about 7.8:1 to about 20:1, from about 8:1 to about 15:1, from about 8.4:1 to about 14:1, or about 9:1 to about 12:1.

Additionally, in yet other alternative embodiments (e.g., concentrate or ready-to-use compositions), wherein for example picloram is used, the ratio of glyphosate to pyridine analog (e.g., picloram) may be greater than about 1:1 and less than about 32:1, range for example from about 5:1 to about 30:1, from about 10:1 to about 25:1, from about 11:1 to about 20:1, from about 12:1 to about 18:1, or from about 14:1 to about 16:1.

In view of the foregoing, and as further described elsewhere herein, it is to be noted that the concentration of glyphosate, the concentration of the pyridine analog (e.g., triclopyr, clopyralid, fluoroxypyr, dithiopyr, thiazopyr, picloram, etc., or a combination thereof), the weight ratio of glyphosate to the pyridine analog, and/or the various ranges associated therewith, may be other than herein described without departing from the scope of the present invention.

It is to be further noted that the various concentrations of the pyridine analog provided herein, as well as the various ratios of glyphosate to the pyridine analog, are intended to apply independently to each analog; that is, although not specifically recited, it is to be noted that each concentration, concentration range, ratio, etc. noted herein is intended to apply independently triclopyr, clopyralid, fluoroxypyr, dithiopyr, thiazopyr, picloram, etc., or a combination thereof.

II. SURFACTANTS

Various surfactants may be effective in formulating the herbicidal compositions or concentrates of the present invention, including for example the nonionic, cationic, anionic and amphoteric surfactants as described below, as well as mixtures thereof.

Cationic surfactants effective in such glyphosate compositions or formulations include, for example:

(a) a secondary or tertiary amine having the formula:

(1)

wherein $R^1$ and $R^2$ are hydrocarbyl having from 1 to about 30 carbon atoms, and $R^3$ is hydrogen or hydrocarbyl having from 1 to about 30 carbon atoms. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$ and $R^3$ are independently hydrogen or a linear or branched alkyl or linear or branched alkenyl group having from 1 to about 6 carbon atoms. More preferably, $R^1$ is a linear or branched alkyl group having from about 12 to about 22 carbon atoms, and $R^2$ and $R^3$ are independently hydrogen, methyl, ethyl, or linear or branched hydroxyalkyl groups having from 1 to about 6 carbon atoms.

In an alternative embodiment, the surfactant may have the formula (1) wherein $R^1$ is hydrocarbyl or substituted hydrocarbyl having from about 8 to about 30 carbon atoms, $R^2$ is a hydroxyalkyl, polyhydroxyalkyl or poly(hydroxyalkyl)alkyl group, and $R^3$ is hydrogen, hydroxyalkyl, polyhydroxyalkyl or poly(hydroxyalkyl)alkyl. In this context, preferred $R^1$ hydrocarbyl groups are linear or branched alkyl, linear or branched alkenyl, linear or branched alkynyl, aryl, or aralkyl groups. In one embodiment, $R^1$ is a linear or branched alkyl, linear or branched alkenyl, linear or branched alkynyl, aryl, or aralkyl group having from about 8 to about 30 carbon atoms, $R^2$ is a linear or branched hydroxyalkyl group having from 1 to about 6 carbon atoms, and $R^3$ is hydrogen or a linear or branched hydroxyalkyl group having from 1 to about 6 carbon atoms. Preferably, $R^1$ is a linear or branched alkyl, linear or branched alkenyl, linear or branched alkynyl, aryl, or aralkyl group having from about 8 to about 22 carbon atoms, $R^2$ is a linear or branched hydroxyalkyl group having from 1 to about 4 carbon atoms, and $R^3$ is hydrogen or a linear or branched hydroxyalkyl group having from 1 to about 4 carbon atoms. More preferably, $R^1$ is a linear or branched alkyl, linear or branched alkenyl, linear or branched alkynyl, aryl, or aralkyl group having from about 8 to about 18 carbon atoms, $R^2$ is hydroxymethyl or hydroxyethyl, and $R^3$ is hydrogen, hydroxymethyl or hydroxyethyl.

(b) a monoalkoxylated amine having the formula:

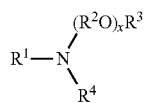

(2)

wherein $R^1$ and $R^4$ are independently hydrocarbyl or substituted hydrocarbyl groups having from 1 to about 30 carbon atoms or —$R^5SR^6$, $R^2$ in each of the x ($R^2O$) groups is independently $C_2$-$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60. In this context, preferred $R^1$, $R^4$, and $R^6$ hydrocarbyl groups are linear or branched alkyl, linear or branched alkenyl, linear or branched alkynyl, aryl, or aralkyl groups. In one embodiment, $R^1$ includes from about 7 to about 30 carbon atoms, preferably from about 8 to about 22 carbon atoms, and the remaining groups are as described above. Preferably, $R^1$ and $R^4$ are independently a linear or branched alkyl or linear or branched alkenyl group having from 1 to about 25 carbon atoms, $R^2$ in each of the x ($R^2O$) groups is independently $C_2$-$C_4$ alkylene, $R^3$ is hydrogen, methyl or ethyl, and x is an average number from 1 to about 40. More preferably, $R^1$ and $R^4$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) groups is independently ethylene or propylene, $R^3$ is hydrogen or methyl, and x is an average number from about 1 to about 10. Most preferably, $R^1$ is a linear or branched alkyl group having from about 16 to about 22 carbon atoms and $R^4$ is methyl, $R^2$ in each of the x ($R^2O$) groups is ethylene, $R^3$ is hydrogen, and x is an average number from about 1 to about 5, or $R^1$ is a linear or branched alkyl group having from about 8 to about 15 carbon atoms and $R^4$ is methyl, $R^2$ in each of the x ($R^2O$) groups is ethylene, $R^3$ is hydrogen, and x is an average number from about 5 to about 10.

(c) a dialkoxylated quaternary ammonium salt having the formula:

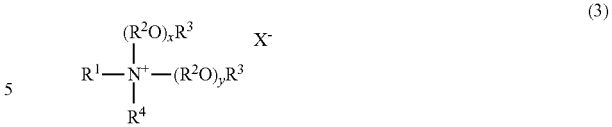

(3)

wherein $R^1$ is hydrocarbyl or substituted hydrocarbyl having from 1 to about 30 carbon atoms, $R^2$ in each of the x ($R^2O$) and y ($R^2O$) groups is independently $C_2$-$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X— is an agriculturally acceptable anion. In this context, preferred $R^1$ and $R^4$ hydrocarbyl groups are linear or branched alkyl, linear or branched alkenyl, linear or branched alkynyl, aryl, or aralkyl groups. Preferably, $R^1$ and $R^4$ are independently a linear or branched alkyl or linear or branched alkenyl group having from 1 to about 25 carbon atoms, $R^2$ in each of the x ($R^2O$) and y ($R^2O$) groups is independently $C_2$-$C_4$ alkylene, $R^3$ is hydrogen, methyl or ethyl, and the sum of x and y is an average number from about 2 to about 30. More preferably, $R^1$ and $R^4$ are independently a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x and y is an average number from about 2 to about 20. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x and y is an average number from about 2 to about 20. Most preferably, $R^1$ is a linear or branched alkyl group having from about 8 to about 22 carbon atoms and $R^4$ is a linear or branched alkyl group having from 1 to about 6 carbon atoms, $R^2$ in each of the x ($R^2O$) and y ($R^2O$) groups is independently ethylene or propylene, $R^3$ is hydrogen or methyl, and the sum of x and y is an average number from about 2 to about 15, or $R^1$ and $R^4$ are independently a linear or branched alkyl group having from about 8 to about 22 carbon atoms, $R^2$ in each of the x ($R^2O$) and y ($R^2O$) groups is independently ethylene or propylene, $R^3$ is hydrogen or methyl, and the sum of x and y is an average number from about 5 to about 15. Preferred dialkoxylated quaternary ammonium surfactants include Ethoquad™ C12 (a PEG 2 coco methyl ammonium chloride from Akzo Nobel), PEG 5 coco methyl ammonium chloride, PEG 5 tallow methyl ammonium chloride, PEG 5 ditallow ammonium bromide, and PEG 10 ditallow ammonium bromide.

(d) a monoalkoxylated quaternary ammonium salt having the formula:

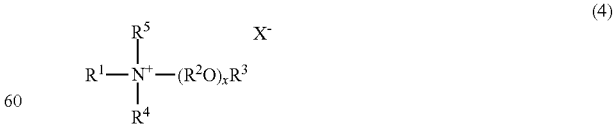

(4)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 30 carbon atoms, x is an average number from 1 to about 60, and X— is an agriculturally acceptable anion. In this context, preferred $R^1$, $R^4$, and $R^5$ hydrocarbyl groups are linear or branched alkyl, linear or branched alkenyl, linear or branched alkynyl, aryl, or aralkyl groups. Preferably, $R^1$, $R^4$ and $R^5$ are independently a linear or branched alkyl or linear or branched alkenyl group having from 1 to about 25 carbon atoms, $R^2$ in each of the x ($R^2O$) groups is independently $C_2$-$C_4$ alkylene, $R^3$ is hydrogen, methyl or ethyl, and x is an average number from 1 to about 40. More preferably, $R^1$, $R^4$ and $R^5$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 22 carbon atoms, and x is an average number from 1 to about 30. Even more preferably, $R^1$ is a linear or branched alkyl group having from about 8 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 6 carbon atoms, and x is an average number from about 5 to about 25. Most preferably, $R^1$ is a linear or branched alkyl group having from about 16 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 3 carbon atoms, and x is an average number from about 5 to about 25. Preferred monoalkoxylated quaternary ammonium surfactants include PEG 7 $C_{18}$ dimethyl ammonium chloride and PEG 22 $C_{18}$ dimethyl ammonium chloride.

(e) a quaternary ammonium salt having the formula:

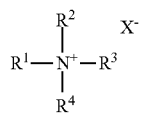

(5)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X— is an agriculturally acceptable anion. In this context, preferred $R^1$, $R^2$, $R^3$, and $R^4$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$, $R^3$ and $R^4$ are independently a linear or branched alkyl or linear or branched alkenyl group having from 1 to about 30 carbon atoms. More preferably, $R^1$ is a linear or branched alkyl or linear or branched alkenyl group having from about 8 to about 22 carbon atoms, and $R^2$, $R^3$ and $R^4$ are independently a linear or branched alkyl or linear or branched alkenyl group having from 1 to about 6 carbon atoms. Even more preferably, $R^1$ is a linear or branched alkyl group having from about 8 to about 16 carbon atoms, and $R^2$, $R^3$ and $R^4$ are independently a linear or branched alkyl group having from 1 to about 6 carbon atoms. Most preferably, $R^1$ is a linear or branched alkyl group having from about 8 to about 14 carbon atoms, and $R^2$, $R^3$ and $R^4$ are methyl. Preferred commercially available quaternary ammonium surfactants include Arquad™ C-50 (a dodecyl trimethyl ammonium chloride from Akzo Nobel) and Arquad™ T-50 (a tallow trimethyl ammonium chloride from Akzo Nobel).

(f) an ether amine having the formula:

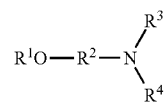

(6)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —$(R^5O)_xR^6$, $R^5$ in each of the $x(R^5—O)$ groups is independently $C_2$-$C_4$ alkylene, $R^6$ is hydrogen, or a linear or branched alkyl group having from 1 to about 4 carbon atoms, and x is an average number from 1 to about 50. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl, linear or branched alkenyl, linear or branched alkynyl, aryl, or aralkyl group having from 8 to about 25 carbon atoms, $R^2$ is a linear or branched alkylene or alkenylene group having from 2 to about 30 carbon atoms, $R^3$ and $R^4$ are independently hydrogen, a linear or branched alkyl, linear or branched alkenyl, linear or branched alkynyl, aryl, or aralkyl group having from 1 to about 30 carbon atoms, or —$(R^5O)_xR^6$, $R^5$ in each of the x ($R^5O$) groups is independently $C_2$-$C_4$ alkylene, $R^6$ is hydrogen, methyl or ethyl, and x is an average number from 1 to about 30. More preferably, $R^1$ is a linear or branched alkyl or alkenyl group having from 8 to about 22 carbon atoms, $R^2$ is a linear or branched alkylene or alkenylene group having from 2 to about 6 carbon atoms, $R^3$ and $R^4$ are independently hydrogen, a linear or branched alkyl or alkenyl group having from 1 to about 6 carbon atoms, or —$(R^5O)_xR^6$, $R^5$ in each of the x ($R^5O$) groups is independently ethylene or propylene, $R^6$ is hydrogen or methyl, and x is an average number from 1 to about 15. Most preferably, $R^1$ is a linear or branched alkyl or alkenyl group having from 8 to about 18 carbon atoms, $R^2$ is ethylene or propylene, $R^3$ and $R^4$ are independently hydrogen, methyl, or —$(R^5O)_xR^6$, $R^5$ in each of the x ($R^5O$) groups is independently ethylene or propylene, $R^6$ is hydrogen, and x is an average number from 1 to about 5.

(g) a diamine having the formula:

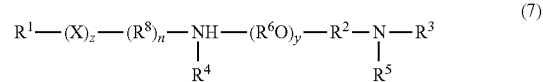

(7)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$; $R^2$ and $R^8$ are independently hydrocarbylene or substituted hydrocarbylene having from 2 to about 30 carbon atoms, $R^6$ in each of the x ($R^6O$) and y ($R^6O$) groups is independently $C_2$-$C_4$ alkylene, $R^7$ is hydrogen, or a linear or branched alkyl group having from 1 to about 30 carbon atoms, x is an average number from 1 to about 30, X is —O—, —N(R⁶)—, —C(O)—, —C(O)O—, —OC(O)—, —N(R⁹)C(O)—, —C(O)N(R⁹)—, —S—, —SO—, or —SO₂—, y is 0 or an average number from 1 to about 30, n and z are independently 0 or 1, and R⁹ is hydrogen or hydrocarbyl or substituted hydrocarbyl. In this context, preferred $R^1$, $R^2$, $R^3$, $R^4$, $R^5$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^4$ are independently a linear or branched alkyl or linear or branched alkenyl group having from about 1 to about 22 carbon atoms, $R^2$ and $R^8$ are independently linear or branched alkylene groups having from about 2 to about 25 carbon atoms, $R^3$ and $R^5$ are each independently hydrogen or a linear or branched alkyl group having from 1 to about 6 carbon atoms and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 8 to about 25 carbon atoms, and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 1 to about 6 carbon atoms, $R^6$ in each of the y ($R^6O$) groups is independently $C_2$-$C_4$ alkylene, y is an average number from 1 to about 20 and n and z are 0; or $R^1$ and $R^3$ are independently a linear or branched alkyl or linear or branched alkenyl group having from about 8 to about 22 carbon atoms, $R^2$ is a linear or branched alkylene group having from about 2 to about 25 carbon atoms; and $R^4$ and $R^5$ are each independently hydrogen, a linear or branched alkyl or alkenyl group having from 1 to about 6 carbon atoms, or —($R^6O$)$_x$$R^7$, $R^6$ in each of the x ($R^6O$) groups is independently $C_2$-$C_4$ alkylene, $R^7$ is hydrogen, or a linear or branched alkyl group having from 1 to about 4 carbon atoms, x is an average number from 1 to about 30, and n, y and z are 0; or $R^1$ is a linear or branched alkyl or linear or branched alkenyl group having from about 1 to about 22 carbon atoms, $R^2$ is a linear or branched alkylene group having from about 2 to about 25 carbon atoms, $R^3$, $R^4$ and $R^5$ are each independently hydrogen or a linear or branched alkyl group having from 1 to about 6 carbon atoms, X is —C(O)— or —SO₂—, n and y are 0 and z is 1. More preferably, $R^1$ and $R^4$ are independently a linear or branched alkyl or linear or branched alkenyl group having from about 4 to about 18 carbon atoms, $R^2$ is a linear or branched alkylene group having from about 2 to about 6 carbon atoms, $R^3$ and $R^5$ are each independently hydrogen or a linear or branched alkyl group having from 1 to about 6 carbon atoms, and n, y and z are 0; or $R^1$, $R^2$, $R^3$ and $R^4$ are independently hydrogen or a linear or branched alkyl group having from about 1 to about 6 carbon atoms, $R^2$ is a linear or branched alkylene group having from about 8 to about 25 carbon atoms, and y is 0; or $R^1$, $R^2$, $R^3$ and $R^4$ are independently hydrogen or a linear or branched alkyl group having from about 1 to about 6 carbon atoms, $R^2$ is a linear or branched alkylene group having from about 1 to about 6 carbon atoms, $R^6$ in each of the y ($R^6O$) groups is independently ethylene or propylene, y is an average number from 1 to about 10 and n and z is 0; or $R^1$ and $R^3$ are independently a linear or branched alkyl group having from about 8 to about 22 carbon atoms, $R^2$ is a linear or branched alkylene group having from about 2 to about 6 carbon atoms, and $R^4$ and $R^5$ are each independently hydrogen, a linear or branched alkyl group having from 1 to about 6 carbon atoms, or —($R^6O$)$_x$$R^7$, $R^6$ in each of the x ($R^6O$) groups is independently ethylene or propylene, $R^7$ is hydrogen or methyl, x is an average number from 1 to about 15, and n, y and z are 0; or $R^1$ is a linear or branched alkyl group having from about 1 to about 22 carbon atoms, $R^2$ is a linear or branched alkylene group having from about 2 to about 6 carbon atoms, $R^3$, $R^4$ and $R^5$ are each independently hydrogen, X is —C(O)— or —SO₂—, n and y are 0 and z is 1. Preferred diamines include Gemini 14-2-14, Gemini 14-3-14, Gemini 10-2-10, Gemini 10-3-10, Gemini 10-4-10, and Gemini 16-2-16 ($C_{10}$, $C_{14}$ or $C_{16}$ ethylene, propylene or butylene N-methyl diamines from Monsanto), Ethoduomeens™, and Jeffamine™ EDR-148.

(h) an amine oxide having the formula:

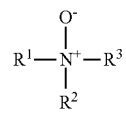

(8)

wherein $R^1$, $R^2$ and $R^3$ are independently hydrogen, hydrocarbyl or substituted hydrocarbyl, —($R^4O$)$_x$$R^5$, or —$R^6$(O$R^4$)$_x$O$R^5$; $R^4$ in each of the x ($R^4O$) groups is independently $C_2$-$C_4$ alkylene, $R^5$ is hydrogen, or a linear or branched alkyl group having from 1 to about 30 carbon atoms, $R^6$ is hydrocarbylene or substituted hydrocarbylene having from 2 to about 6 carbon atoms, x in each of the x ($R^4O$) groups is independently an average number from 1 to about 50, and the total number of carbon atoms in $R^1$, $R^2$ and $R^3$ is at least 8. In this context, preferred $R^1$, $R^2$, $R^3$, and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^2$ are independently hydrogen, a linear or branched alkyl or linear or branched alkenyl group having from 1 to about 30 carbon atoms, or —($R^4O$)$_x$$R^5$; $R^3$ is a linear or branched alkyl or linear or branched alkenyl group having from about 8 to about 30 carbon atoms, $R^4$ in each of the x ($R^4O$) groups is independently $C_2$-$C_4$ alkylene; $R^5$ is hydrogen, methyl or ethyl, and x is an average number from 1 to about 30. More preferably, $R^1$ and $R^2$ are independently hydrogen, or a linear or branched alkyl group having from 1 to about 6 carbon atoms, and $R^3$ is a linear or branched alkyl group having from about 8 to about 22 carbon atoms; or $R^1$ and $R^2$ are independently —($R^4O$)$_x$$R^5$, $R^3$ is a linear or branched alkyl group having from about 8 to about 22 carbon atoms, $R^4$ in each of the x ($R^4O$) groups is ethylene or propylene, $R^5$ is hydrogen or methyl, and x is an average number from 1 to about 10. Most preferably, $R^1$ and $R^2$ are independently methyl, and $R^3$ is a linear or branched alkyl group having from about 8 to about 18 carbon atoms; or $R^1$ and $R^2$ are independently —($R^4O$)$_x$$R^5$, $R^3$ is a linear or branched alkyl group having from about 8 to about 18 carbon atoms, $R^4$ in each of the x ($R^4O$) groups is ethylene or propylene, $R^5$ is hydrogen, and x is an average number from 1 to about 5. Commercially available amine oxide surfactants include Chemoxide L70.

(i) a dialkoxylated amine having the formula:

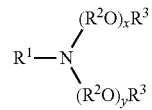

(9)

wherein $R^1$ is a hydrocarbyl or substituted hydrocarbyl having from about 6 to about 30 carbon atoms, or —$R^4$S$R^5$, $R^4$ and $R^2$ in each of the x ($R^2O$) and the y ($R^2O$) groups is independently $C_2$-$C_4$ alkylene, $R^3$ is hydrogen, or a linear or branched alkyl group having from 1 to about 4 carbon atoms, $R^5$ is a linear or branched alkyl group having from about 4 to about 15 carbon atoms, and x and y are independently an average number from 1 to about 40. In this context, preferred $R^1$ hydrocarbyl groups are linear or branched alkyl, linear or branched alkenyl, linear or branched alkynyl, aryl, or aralkyl groups. Preferably, $R^1$ is a linear or branched alkynyl, aryl, or aralkyl group having from about 8 to about 30 carbon atoms, $R^2$ in each of the x ($R^2O$) and the y ($R^2O$) groups is independently $C_2$-$C_4$ alkylene, $R^3$ is hydrogen, methyl or ethyl, and x and y are independently an average number from 1 to about 20. More preferably, $R^1$ is a linear or branched alkynyl, aryl, or aralkyl group having from about 8 to about 25 carbon atoms, $R^2$ in each of the x ($R^2O$) and the y ($R^2O$) groups is independently ethylene or propylene, $R^3$ is hydrogen or methyl, and x and y are independently an average number from 1 to about 30. Even more preferably, $R^1$ is a linear or branched alkynyl, aryl, or aralkyl group having from about 8 to about 22, or about 12 to about 22, carbon atoms, $R^2$ in each of the x ($R^2O$) and the y ($R^2O$) groups is independently ethylene or propylene, $R^3$ is hydrogen or methyl, and x and y are independently an average number from 1 to about 5. Some commercially available dialkoxylated amines include, for example, Trymeen™ 6617 (from Cognis) and Ethomeen™ C/12, C/15, C/20, C/25, T/12, T/15, T/20 and T/25 (from Akzo Nobel).

and (j) an aminated alkoxylated alcohol having the formula:

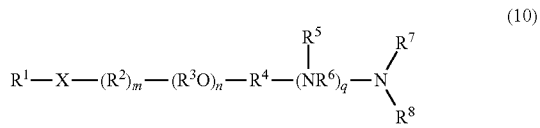

(10)

wherein $R^1$, $R^7$, $R^8$, and $R^9$ are each independently hydrogen, hydrocarbyl or substituted hydrocarbyl having from 1 to about 30 carbon atoms, or —($R^{11}$)$_s$($R^3O$)$_v$$R^{10}$; X is —O—, —OC(O)—, —C(O)O—, —N($R^{12}$)C(O)—, —C(O)N($R^{12}$)—, —S—, —SO—, —SO$_2$— or —N($R^9$)—; $R^3$ in each of the n ($R^3O$) groups and the v ($R^3O$) groups is independently $C_2$-$C_4$ alkylene; $R^{10}$ is hydrogen, or a linear or branched alkyl group having from 1 to about 30 carbon atoms; n is an average number from 1 to about 60; v is an average number from 1 to about 50; $R^2$ and $R^{11}$ are each independently hydrocarbylene or substituted hydrocarbylene having from 1 to about 6 carbon atoms; $R^4$ is hydrocarbylene or substituted hydrocarbylene having from 2 to about 6 carbon atoms; $R^{12}$ is hydrogen or hydrocarbyl or substituted hydrocarbyl having from 1 to about 30 carbon atoms; m and s are each independently 0 or 1; $R^6$ is hydrocarbylene or substituted hydrocarbylene having from 2 to about 30 carbon atoms, —C(=N$R^{12}$)—, —C(S)—, or —C(O)—; q is an integer from 0 to 5; and $R^5$ is hydrogen or hydrocarbyl or substituted hydrocarbyl having from 1 to about 30 carbon atoms. In this context, preferred $R^1$, $R^2$, $R^4$, $R^5$, $R^6$, $R^7$, $R^8$, $R^9$, $R^{11}$ and $R^{12}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

A subclass of such cationic surfactants includes monoalkoxylated amines having the formula:

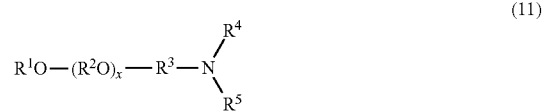

(11)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ is hydrocarbylene or substituted hydrocarbylene having from 2 to about 30 carbon atoms; $R^4$ and $R^5$ are each independently hydrogen, hydrocarbyl or substituted hydrocarbyl having from 1 to about 30 carbon atoms, —($R^6$)$_n$—($R^2O$)$_y$$R^7$, or $R^4$ and $R^5$, together with the nitrogen atom to which they are attached, form a cyclic or heterocyclic ring; $R^6$ is hydrocarbylene or substituted hydrocarbylene having from 1 to about 30 carbon atoms; $R^7$ is hydrogen or a linear or branched alkyl group having 1 to about 4 carbon atoms, n is 0 or 1, x and y are independently an average number from 1 to about 60. In this context, preferred $R^1$, $R^3$, $R^4$, $R^5$, and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2$-$C_4$ alkylene, $R^3$ is a linear or branched alkylene group having from 2 to about 20 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is ethylene or propylene, $R^4$ and $R^5$ are each independently hydrogen, methyl or tris(hydroxymethyl)methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is ethylene, $R^4$ and $R^5$ are methyl, and x is an average number from about 4 to about 20. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 15 or 20 or 25 $C_{16-18}$ ether dimethyl propylamines (from Tomah) and Surfonic™ AGM-550 from Huntsman.

Quaternary ammonium, sulfonium and sulfoxonium salts are also effective cationic surfactants in forming glyphosate concentrates and have the chemical structures:

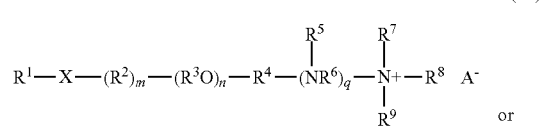

(12)

or

-continued

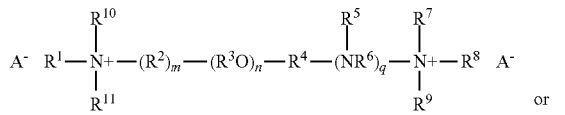

(13)

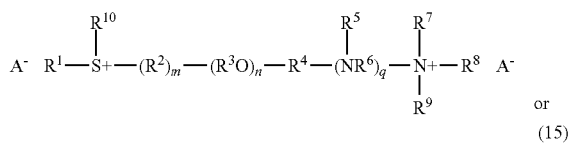

or (14)

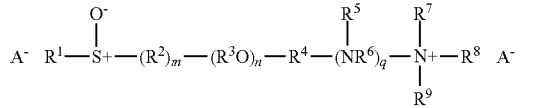

(15)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or —$(R^{13})_s(R^3O)_vR^{12}$; X is —O—, —OC(O)—, —N($R^{14}$)C(O)—, —C(O)N($R^{14}$)—, —C(O)O—, or —S—; $R^3$ in each of the n ($R^3O$) groups and v ($R^3O$) groups is independently $C_2$-$C_4$ alkylene; $R^{12}$ is hydrogen, or a linear or branched alkyl group having from 1 to about 30 carbon atoms; n is an average number from 1 to about 60; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, —C(=$NR^{12}$)—, —C(S)—, or —C(O)—; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each $A^-$ is an agriculturally acceptable anion. In this context, preferred $R^1$, $R^2$, $R^4$, $R^5$, $R^6$, $R^7$, $R^8$, $R^9$, $R^{10}$, $R^{11}$, $R^{13}$, and $R^{14}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

Other cationic surfactants effective in any glyphosate composition or formulation are diamines or diammonium salts having the formulas:

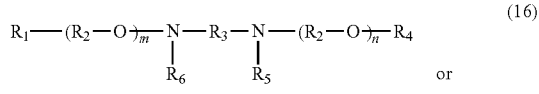

(16)

or

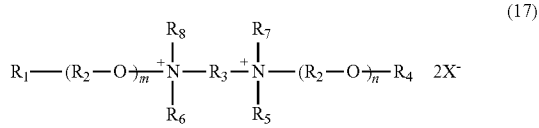

(17)

wherein $R_1$, $R_4$, $R_5$, $R_6$, $R_7$ and $R_8$ are independently hydrogen or hydrocarbyl or substituted hydrocarbyl having from 1 to about 30 carbon atoms, $R_2$ in each of the m ($R^2O$) and n ($R^2O$) groups and $R_9$ are independently $C_2$-$C_4$ alkylene, $R_3$ is hydrocarbylene or substituted hydrocarbylene having from about 2 to about 6 carbon atoms or —$(R^2O)_pR_9$—, m and n are individually an average number from 0 to about 50, and p is an average number from 0 to about 60. In this context, preferred $R^1$, $R^3$, $R^4$, $R^5$, $R^6$, $R^7$ and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment of formula (DA), $R^3$ is hydrocarbylene having from about 2 to about 6 carbon atoms, and the remaining groups are as defined above.

Preferred nonionic surfactants for such glyphosate concentrates include alkoxylated alcohols having the formula:

(18)

wherein $R^1$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 4 carbon atoms, and x is an average number from 1 to about 60. In this context, preferred $R^1$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ in each of the x ($R^2O$) groups is independently $C_2$-$C_4$ alkylene, $R^3$ is hydrogen, methyl or ethyl, and x is an average number from about 5 to about 50. More preferably, $R^1$ is a linear or branched alkyl group having from about 8 to about 25 carbon atoms, $R^2$ in each of the x ($R^2O$) groups is independently ethylene or propylene, $R^3$ is hydrogen or methyl, and x is an average number from about 8 to about 40. Even more preferably, $R^1$ is a linear or branched alkyl group having from about 12 to about 22 carbon atoms, $R^2$ in each of the x ($R^2O$) groups is independently ethylene or propylene, $R^3$ is hydrogen or methyl, and x is an average number from about 8 to about 30. Preferred commercially available alkoxylated alcohols include Procol™ LA-15 (from Protameen), Brij™ 35, Brij™ 76, Brij™ 78, Brij™ 97 and Brij™ 98 (from Sigma Chemical Co.), Neodol™ 25-12 (from Shell), Hexotol™ CA-10, Hexotol™ CA-20, Hexotol™ CS-9, Hexotol™ CS-15, Hexotol™ CS-20, Hexotol™ CS-25, Hexotol™ CS-30, and Plurafac™ A38 (from BASF), ST-8303 (from Cognis), and Arosurf™ 66 E20 (from Witco/Crompton).

Other nonionic surfactants for use in such glyphosate compositions or formulations include alkoxylated dialkylphenols having the formula:

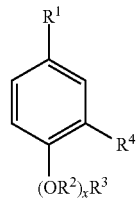

(19)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^2O$) groups is independently $C_2$-$C_4$ alkylene, $R^3$ is hydrogen, or a linear or branched alkyl group having from 1 to about 4 carbon atoms, and x is an average number from 1 to about 60. Preferably, $R^1$ and $R^4$ are independently linear or branched alkyl groups having from 8 to about 30 carbon atoms, $R^2$ in each of the x ($R^2O$) groups is independently $C_2$-$C_4$ alkylene, $R^3$ is hydrogen, methyl or ethyl, and x is an average number from about 5 to about 50. More preferably, $R^1$ and $R^4$ are independently linear or branched alkyl groups having from about 8 to about 22 carbon atoms, $R^2$ in each of the x ($R^2O$) groups is independently ethylene or propylene, $R^3$ is hydrogen or methyl, and x is an average number from about 8 to about 40. Even more preferably, $R^1$ and $R^4$ are independently linear or branched alkyl groups having from about 8 to about 16 carbon atoms, $R^2$ in each of the x ($R^2O$) groups is independently ethylene or propylene, $R^3$ is hydrogen or methyl, and x is an average number from about 10 to about 30. Preferred commercially available alkoxylated dialkylphenols include ethoxylated dinonyl phenols such as Surfonic™ DNP 100, Surfonic™ DNP 140, and Surfonic™ DNP 240 (from Huntsman).

Preferred anionic surfactants effective in forming glyphosate compositions or formulations, in at least some embodiments, may include saturated carboxylic acids such as butyric, caproic, caprylic, capric, lauric, palmitic, myristic or stearic acid, and unsaturated carboxylic acids such as palmitoleic, oleic, linoleic or linolenic acid. Preferred carboxylic acids, in at least some embodiments, may include palmitic, oleic or stearic acid. Other preferred anionic surfactants, in at least some embodiments, may include alkyl sulfates such as sodium lauryl sulfate, and alkyl alkoxylated phosphates having the formulae:

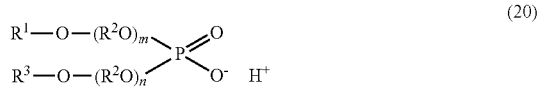
(20)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$-$C_4$ alkylene; and m and n are independently from 1 to about 30; or

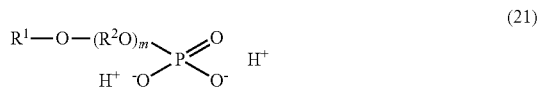
(21)

wherein $R^1$ is a linear or branched alkyl, linear or branched alkenyl, linear or branched alkynyl, aryl, or aralkyl group having from about 8 to about 30 carbon atoms; $R^2$ in each of the m ($R^2O$) groups is independently $C_2$-$C_4$ alkylene; and m is from 1 to about 30. Representative alkyl alkoxylated phosphates include oleth-10 phosphate, oleth-20 phosphate and oleth-25 phosphate. Other representative alkyl alkoxylated phosphates include those wherein, in (21), $R^1$ has about 10 to about 15 carbon atoms, $R^2$ is ethylene or propylene, and m is from about 1 to about 10, from about 2 to about 8, or about 4 to about 6.

Other exemplary surfactants that may be used in accordance with the present invention include the following species:

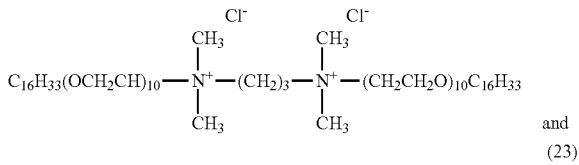
(22)

and

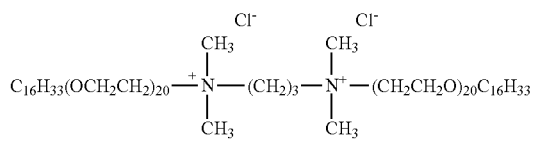
(23)

In at least some embodiments of one or more of the aqueous or dry concentrates, or alternatively the ready-to-use composition, described herein, the weight ratio of glyphosate (a.e. basis) to surfactant may range from about 1:10 to 10:1 or more (e.g., from about 1:8 to 8:1, from about 1:6 to about 6:1, from about 1:4 to about 4:1, from about 1:3 to about 3:1, or from about 1:2 to about 2:1). Alternatively, this ratio may range from about 1:1 to about 10:1 (e.g., from about 1:1 to about 10:1, from about 2:1 to about 8:1, or from about 3:1 to about 6:1), from about 1:1 to about 15:1, from about 1:1 to about 20:1, or more. Accordingly, exemplary ratios include about 1:10, about 1:9.5, about 1:9, about 1:8.5, about 1:8, about 1:7.5, about 1:7, about 1:6.5, about 1:6, about 1:5.5, about 1:5, about 1:4.5, about 1:4, about 1:3.5, about 1:3, about 12.5, about 1:2, about 1:1.5, about 1:1, about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, about 10:1, about 11:1, about 12:1, about 13:1, about 14:1, about 15:1, about 16:1, about 17:1, about 18:1, about 19:1, about 20:1 or more.

Alternatively, in these or other embodiments (e.g, a ready-to-use composition), the weight ratio of glyphosate (a.e. basis) to surfactant may range from about 10:1 to about 1:5 (e.g., from about 8:1 to about 1:4, from about 6:1 to about 1:3, from about 4:1 to about 1:2, or from about 2:1 to about 1:1).

Additionally, in these or other embodiments, the surfactant concentration may be at least about 1 gram per liter (e.g., at least about 5, 10, 20, 30, 40, 50, 60, 70, 80, 90, 100, 125, 150, 200, 250, 300, 350, 400, 450, 500 grams per liter or more), ranging for example from about 1 to about 500 grams per liter, from about 5 to about 250 grams per liter, 10 to about 100 grams per liter, from about 20 to about 80 grams per liter, or from about 40 to about 60 grams per liter. Alternatively, the surfactant concentration may range from about 1 to 283 grams per liter (e.g., ranging for example from about 1 to about 275 grams per liter, from about 5 to about 250 grams per liter, from about 10 to about 100 grams per liter, from about 20 to about 80 grams per liter, or from about 40 to about 60 grams per liter).

In some embodiments (e.g., a ready-to-use composition), the surfactant concentration may not be greater than 3.9 grams per liter (e.g., not greater than 3.8, 3.6, 3.4, 3.2, 3, 2.8, 2.6, 2.4, 2.2, 2, 1.8, 1.6, 1.4, 1.2, 1 or less), when the weight ratio (a.e. to a.e.) of glyphosate to pyridine analog (triclopyr, for example) is at least 3:1. In these or other embodiments, the surfactant concentration may not be greater than 6.6 grams per liter (e.g., not greater than 6.4, 6.2, 6, 5.8, 5.6, 5.4, 5.2, 5, 4.8, 4.6, 4.4, 4.2, 4, 3.8, etc.), when the weight ratio (a.e. to a.e.) of glyphosate to pyridine analog (triclopyr, for example) is at least 5:1. In these or still other embodiments, the surfactant concentration may not be greater than 9.3 grams per liter (e.g., not greater than 9.2, 9. 8.8, 8.6, 8.4, 8.2, 8, 7.8, 7.6, 7.4, 7.2, 7, 6.8, 6.6, 6.4, etc.), when the weight ratio (a.e. to a.e.) of glyphosate to pyridine analog (triclopyr, for example) is at least 7:1.

III. PROPERTIES

Among the various properties of the compositions of the present invention is to be noted that these compositions typically have a cloud point of at least about 50° C., or even about 60° C. Additionally, the aqueous concentrate and/or the ready-to-use composition of the present invention typically has a composition such that triclopyr (or more generally the pyridine analog) will not crystallize or precipitate when the bulk solution freezes or solidifies, and then thaws; stated another way, the herbicide compositions or formulations of the present invention have a composition wherein the pyridine analog, such as triclopyr, will not precipitate upon being cooled to a temperature of about 0° C., or even about −10° C.

IV. OPTIONAL ADDITIVES

As further discussed herein, other additives, adjuvants, or ingredients may be introduced into the compositions or formulations of the present invention to improve certain properties thereof (e.g., solubility of the pyridine analog). Although the compositions or formulations of the present invention generally show good overall stability and viscosity properties without the addition of any further additives, the addition of a solubilizer (also commonly referred to as a cloud point enhancer or stabilizer) may significantly improve the properties of the compositions or formulations of the present invention. Suitable solubilizers for use with the novel compositions or formulations of the present invention include, for example, cocoamine (Armeen C), dimethylcocoamine (Arquad DMCD), cocoammonium chloride (Arquad C), PEG 2 cocoamine (Ethomeen C12), a cocodiamine 3EO (Ethoduomeen CD/13), PEG 5 tallowamine (Ethomeen T15), and PEG 5 cocoamine (Ethomeen C15), all of which are manufactured by Akzo Nobel (California).

Additionally, it has been found that the addition of a $C_4$ to $C_{16}$ alkyl or aryl amine compound, or the corresponding quaternary ammonium compound, greatly enhances the compatibility of certain glyphosate salts (e.g., potassium or isopropylamine) with surfactants that otherwise exhibit low or marginal compatibility at a given glyphosate loading. Suitable alkyl or aryl amine compounds may also contain 0 to about 5 EO groups. Preferred alkylamine compounds include $C_6$ to $C_{12}$ alkylamines having 0 to 2 EO groups. Similarly, etheramine compounds having 4 to 12 carbons and 0 to about 5 EO groups, as well as the corresponding quaternary ammonium compounds, also enhance the compatibility of such compositions or formulations. In one embodiment, the compounds which enhance the compatibility of such surfactants include amines or quaternary ammonium salts having the formula:

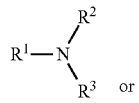

(24)

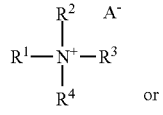

(25)

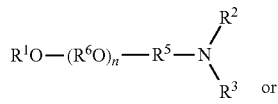

(26)

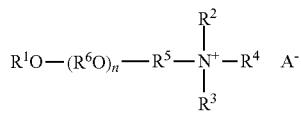

(27)

wherein $R^1$ is linear or branched alkyl or aryl having from about 4 to about 16 carbon atoms, $R^2$ is hydrogen, methyl, ethyl, or —(CH$_2$CH$_2$O)$_x$H, $R^3$ is hydrogen, methyl, ethyl, or —(CH$_2$CH$_2$O)$_y$H wherein the sum of x and y is not more than about 5; $R^4$ is hydrogen or methyl; $R^6$ in each of the n (R$^6$O) groups is independently $C_2$-$C_4$ alkylene; $R^5$ is hydrocarbylene or substituted hydrocarbylene having from 2 to about 6 carbon atoms; and A- is an agriculturally acceptable anion.

Optionally, one or more of the compositions of the present invention may further comprise one or more additional pesticides, such as for example, water-soluble herbicidal active ingredients, including without restriction water-soluble forms of acifluorfen, asulam, benazolin, bentazon, bialaphos, bispyribac, bromacil, bromoxynil, carfentrazone, chloramben, 2,4-D, 2,4-DB, dalapon, dicamba, dichlorprop, diclofop, difenzoquat, diquat, endothall, fenac, fenoxaprop, flamprop, fluazifop, fluoroglycofen, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, sulfamic acid, 2,3,6-TBA, TCA, acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thifensulfuron, thiobencarb, tiocarbazil, tralkoxydim, triallate, triasulfuron, tribenuron, trietazine, trifluralin, triflusulfuron and vernolate.

Another ingredient that can optionally be added to the glyphosate herbicidal compositions or formulations of the present invention to further improve the herbicidal effectiveness and related herbicidal properties is a di-carboxylic acid or salt of a di-carboxylic acid. Suitable di-carboxylic acids that may be added to the herbicidal compositions or formulations comprising glyphosate or a salt or ester thereof and a surfactant as described herein include, for example, oxalic acid, malonic acid, succinic acid, glutaric acid, maleic acid, adipic acid, and fumaric acid, and combinations or mixtures thereof, with oxalic acid being preferred. Also, in addition to, or in place of the di-carboxylic acid, salts of the aforementioned di-carboxylic acids may be incorporated into the herbicidal formulations of the present invention to improve herbicidal performance. Suitable salts include, for example, alkali metal salts such as potassium salts, alkanolamine salts and lower alkylamine salts. Preferred salts include potassium oxalate, dipotassium oxalate, sodium oxalate, disodium oxalate, diammonium oxalate, diethanolamine oxalate, dimethylamine oxalate, alkanolamine salts of oxalic acid, and lower alkylamine salts of oxalic acid.

Formulations containing a di-carboxylic acid such as oxalic acid or a di-carboxylic acid salt such as potassium oxalate, typically contain a sufficient amount of di-carboxylic acid/di-carboxylic acid salt to enhance the resulting efficacy of the herbicidal formulation. The weight ratio of total surfactant to carboxylic acid/carboxylic acid salt may be, for example, from about 1:1 to about 50:1, about 5:1 to about 40:1, or even about 5:1 to about 20:1. This ratio of total surfactant to carboxylic acid/carboxylic acid salt may significantly enhance the herbicidal performance of the resulting herbicidal formulation.

The di-carboxylic acid or salt thereof which can be added to herbicidal formulations of the present invention to improve efficacy are suitable for use with glyphosate, or salts thereof. Suitable glyphosate salts include those listed above, such as for example the isopropylamine salt, the potassium salt, and the trimethylammonium salt.

In this regard it is to be noted that U.S. patent application Ser. No. 09/988,353 (entitled Pesticide Compositions Containing Oxalic Acid and published on Sep. 5, 2002 under Publication No. US-2002-0123430-A1) is incorporated herein by reference, as well as U.S. patent application Ser. No. 10/653,332 (entitled Process for the Preparation of a Dry Pesticidal Composition Containing a Dicarboxylate Component and filed on Sep. 2, 2003) and U.S. patent application Ser. No. 10/653,047 (entitled Pesticidal Compositions Containing Dicarboxylic Acids and filed on Aug. 29, 2003).

Yet another ingredient that can optionally be added to one or more of the compositions of the present invention is a fatty acid (e.g., a $C_8$ to $C_{12}$ fatty acid). For example, in at least one embodiment the present invention is directed to a composition (e.g., a solid or liquid concentrate, or alternatively a ready-to-use composition) comprising glyphosate (or a derivative thereof), triclopyr or other pyridine analog (or a derivative thereof), a pelargonic acid (or nonanoic acid) or derivative thereof, and a surfactant, such as a linear alcohol ethoxylate.

Excipient ingredients other than the above-defined surfactant component can optionally be present in a composition of the invention, so long as the cloud point and non-crystallization properties of the composition remain in accordance with the invention. Such additional excipient ingredients may include conventional formulation additives such as dyes, thickeners, crystallization inhibitors, antifreeze agents (e.g., glycols, such a ethylene glycol), foam moderating agents (e.g., Antifoam™ or Y-14088 Antifoam™, both available from Crompton Corporation), antidrift agents, compatibilizing agents, antioxidants (e.g., ascorbic acid and sodium sulfite, in order for example to prevent the formation of a nitrosamine), other co-solvents (e.g., N-methylpyrrolidone, DMSO, DMF, propylene carbonate, or ethylene glycol), or some other agent added to lessen or overcome antagonism associated with hard water (e.g., ammonium sulfate, EDTA or a polymeric water conditioner, such as a polyacrylic acid), etc.

V. FORMULATIONS

The herbicidal compositions of the invention can be prepared on site by the end-user shortly before application to the foliage of the vegetation to be killed or controlled by mixing in an aqueous solution (i) glyphosate or a herbicidal derivative thereof, (ii) a pyridine analog, such as triclopyr, or a derivative thereof, and (iii) a suitable surfactant. Such compositions are typically referred to as "tank-mix" compositions. Typically, herbicidal compositions of the present invention that are ready to be applied directly to foliage can be made with a glyphosate concentration as described elsewhere herein. Additionally, such herbicidal compositions can be made with a triclopyr, or some other pyridine analog, at a concentration also as described elsewhere herein. However, it is to be noted that one skilled in the art will recognize that various factors influence the application rate of glyphosate and, for example, triclopyr (or another pyridine analog), required for a desired result. As a result, the concentration of such compositions may be other than as described herein without departing from the scope of the present invention.

Alternatively, the herbicidal compositions of the invention may be provided to the end-user already formulated, either at the desired dilution for application (i.e., "ready-to-use" compositions) or requiring dilution, dispersion, or dissolution in water by the end-user (i.e., "concentrate" compositions, wherein the glyphosate concentration is at least about 50 grams (a.e.) per liter). Such preformulated concentrates can be liquids or particulate solids.

With respect to the particulate solids, or dry formulations, of the present invention, it is to be noted that these may be in the form of powders, pellets, tablets or granules. These dry formulations are typically dispersed or dissolved into water prior to use. Preferably, there are no substantially water insoluble constituents present at substantial levels in the such formulations such that the formulations are substantially water soluble. Dry water-soluble or water-dispersable formulations of the present invention typically comprise the same ratios of glyphosate to triclopyr (G:T), or more generally the same ratios of glyphosate to pyridine analog, and glyphosate to surfactant (G:S), as described elsewhere herein. With respect to the load of the composition ingredients (i.e., glyphosate, triclopyr, or other pyridine analog, and surfactant), as well as the particular ingredients themselves, it is to be noted that the selection of these for a given application may be determined in view of commercial consideration, and using means, known in the art.

In dry formulations of the present invention, the glyphosate itself may provide the support for other formulation constituents, or there may be additional inert ingredients which provide such support. One example of an inert support ingredient that may be used in accordance with the present invention is ammonium sulfate. It will be recognized by one skilled in the art that as used herein, the term "dry" does not imply that dry formulations of the present invention are 100% free of water. Typically, dry formulations of the present invention comprise from about 0.5% to about 5% (by weight) water. It is preferred that the dry formulations of the present invention contain less than about 1% (by weight) water. Additionally, it is preferred for at least some embodiments that the particulate solid exhibits a dissolution rate of not more than about 5 minutes, about 4 minutes, about 3 minutes, about 2 minutes, or even about 1 minute.

Dry, water soluble or water dispersable formulations in accordance with the present invention can be produced by any process known in the art, including spray drying, fluid-bed agglomeration, pan granulation, or extrusion. In dry formulations, glyphosate may be present as a salt, or as an acid. Formulations containing glyphosate acid may optionally contain an acid acceptor such as an ammonium or alkali metal carbonate or bicarbonate, ammonium dihydrogen phosphate or the like so that upon dissolution or dispersion in water by the user a water soluble salt of glyphosate is produced.

Also embraced by the present invention are liquid concentrate formulations having an aqueous phase wherein glyphosate is present predominantly in the form of a salt, and a non-aqueous phase optionally containing a second herbicidal active ingredient that is relatively water-insoluble. Such formulations illustratively include emulsions (including macro- and microemulsions, water-in-oil, oil-in-water and water-in-oil-in-water types), suspensions and suspoemulsions. The non-aqueous phase can optionally comprise a microencapsulated component, for example a microencapsulated herbicide. In formulations of the invention having a non-aqueous phase, the concentration of glyphosate a.e. in the composition as a whole is nonetheless within the ranges recited herein for aqueous concentrate formulations.

Illustrative water-insoluble herbicides that can be used in such formulations include acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thifensulfuron, thiobencarb, tiocarbazil, tralkoxydim, triallate, triasulfuron, tribenuron, trietazine, trifluralin, triflusulfuron and vernolate.

It is to be noted that the herbicidal spray compositions of the present invention are applied as aqueous solutions or dispersions, whether they result from the further dilution of the liquid concentrate or the addition of water to the particulate solid concentrate. However, the term "aqueous," as used herein, is not intended to exclude the presence of some small amount of nonaqueous solvent, so long as the predominant solvent present, other than for example the glycol or glycol ester component of the surfactant composition, is water.

VI. APPLICATION

Generally speaking, the present invention is additionally directed to a method of for killing or controlling weeds or unwanted vegetation which comprises the steps of diluting a liquid concentrate in a convenient amount of water to form a tank mix and applying a herbicidally effective amount of the tank mix to the foliage of the weeds or unwanted vegetation. Similarly included in the invention is the method of killing or controlling weeds or unwanted vegetation comprising the steps of diluting a solid particulate concentrate in a convenient amount of water to form a tank mix and applying a herbicidally effective amount of the tank mix to the foliage of the weeds or unwanted vegetation.

The herbicidal composition of the present invention is applied to plants at a rate sufficient to give the desired biological effects: control of plant growth and early visual symptoms of treatment. The amount of glyphosate and triclopyr, or other pyridine analog, applied to plants in combination generally provides a herbicidally-effective amount of the herbicides. The amount of glyphosate and triclopyr, or other pyridine analogy, applied to plants further is sufficient to provide early visual symptoms of plant treatment without significantly reducing the desired biological effect of the glyphosate. These application rates are usually expressed as amount of glyphosate per unit area treated, e.g. grams per hectare (g/ha). What constitutes a "desired effect" varies according to the standards and practice of those who investigate, develop, market and use compositions. Typically, the amount of the composition applied per unit area to give 85% control of a plant species as measured by growth reduction or mortality is often used to define a commercially effective rate. Early visual symptoms of treatment typically appear no later than about 4 days after treatment, preferably no later than about 3 days after treatment, more preferably no later than about 2 days after treatment, and still more preferably no later than about 1 day after treatment.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention. With respect to the use of glyphosate compositions, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

The herbicidal spray compositions included in the present invention can be applied to the foliage of the plants to be treated through any of the appropriate methods that are well known to those having skill in the art. However, in one embodiment, the herbicidal composition is applied using means other than a helicopter; stated another way, in at least some embodiments the present invention is directed to methods wherein the herbicidal composition is applied using nonaerial means (i.e., ground application techniques. such as a hand sprayer, rope-wick, etc.) or using a fixed-wing aircraft.

Particularly important annual dicotyledonous plant species for control of which a composition of the invention can be used are exemplified without limitation by velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*) and cocklebur (*Xanthium* spp.).

Particularly important annual monocotyledonous plant species for control of which a composition of the invention can be used are exemplified without limitation by wild oat (*Avena fatua*), carpetgrass (*Axonopus* spp.), downy brome (*Bromus tectorum*), crabgrass (*Digitaria* spp.), barnyardgrass (*Echinochloa crus-galls*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial dicotyledonous plant species for control of which a composition of the invention can be used are exemplified without limitation by mugwort (*Artemisia* spp.), milkweed (*Asclepias* spp.), canada thistle (*Cirsium arvense*), field bindweed (*Convolvulus arvensis*) and kudzu (*Pueraria* spp.).

Particularly important perennial monocotyledonous plant species for control of which a composition of the invention can be used are exemplified without limitation by brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial plant species for control of which a composition of the invention can be used are exemplified without limitation by horsetail (*Equisetum* spp.), bracken (*Pteridium aquilinum*), blackberry (*Rubus* spp.) and gorse (*Ulex europaeus*).

If desired, the user can mix one or more adjuvants with a composition of the invention and the water of dilution when preparing the application composition. Such adjuvants can include additional surfactant and/or an inorganic salt such as ammonium sulfate with the aim of further enhancing herbicidal efficacy. However, under most conditions a herbicidal method of use of the present invention gives acceptable efficacy in the absence of such adjuvants.

In a particular contemplated method of use of a composition of the invention, the composition, following dilution in water, is applied to foliage of crop plants genetically transformed or selected to tolerate glyphosate, and simultaneously to foliage of weeds or undesired plants growing in close proximity to such crop plants. This method of use results in control of the weeds or undesired plants while leaving the crop plants substantially unharmed. Crop plants genetically transformed or selected to tolerate glyphosate include those whose seeds are sold by Monsanto Company or under license from Monsanto Company bearing the Roundup Ready® trademark. These include, without restriction, varieties of cotton, soybean, canola, sugar beet, wheat and corn.

Plant treatment compositions can be prepared simply by diluting a concentrate composition of the invention in water. Application of plant treatment compositions to foliage is preferably accomplished by spraying, using any conventional means for spraying liquids, such as spray nozzles, atomizers or the like. Compositions of the invention can be used in precision farming techniques, in which apparatus is employed to vary the amount of pesticide applied to different parts of a field, depending on variables such as the particular plant species present, soil composition, etc. In one embodiment of such techniques, a global positioning system operated with the spraying apparatus can be used to apply the desired amount of the composition to different parts of a field.

VII. DEFINITIONS

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from one to 18 carbon atoms in the principal chain and up to 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are preferably lower alkenyl containing from two to 18 carbon atoms in the principal chain and up to 30 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to 18 carbon atoms in the principal chain and up to 30 carbon atoms. They may be straight or branched chain and include ethynyl, propynyl, butynyl, isobutynyl, hexynyl, and the like.

The terms "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

Unless otherwise indicated, the term "hydroxyalkyl" includes alkyl groups substituted with at least one hydroxy group, and includes bis(hydroxyalkyl)alkyl, tris(hydroxyalkyl)alkyl and poly(hydroxyalkyl)alkyl groups. Preferred hydroxyalkyl groups include hydroxymethyl (—CH$_2$OH), and hydroxyethyl (—C$_2$H$_4$OH), bis(hydroxymethyl)methyl (—CH(CH$_2$OH)$_2$), and tris(hydroxymethyl)methyl (—C(CH$_2$OH)$_3$).

The term "cyclic" as used herein alone or as part of another group denotes a group having at least one closed ring, and includes alicyclic, aromatic (arene) and heterocyclic groups.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like, and non-aromatic heterocyclics such as tetrahydrofuryl, tetrahydrothienyl, piperidinyl, pyrrolidino, etc. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioester, thioether, ketal, acetal, ester and ether.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioether, thioester, ketal, acetal, ester and ether.

The term "acyl," as used herein alone or as part of another group, denotes the moiety formed by removal of the hydroxyl group from the group —COOH of an organic carboxylic acid, e.g., RC(O)—, wherein R is R$^1$, R$^1$O—, R$^1$R$^2$N—, or R$^1$S—, R$^1$ is hydrocarbyl, heterosubstituted hydrocarbyl, or heterocyclo and R$^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

The term "pesticide" includes chemicals and microbial agents used as active ingredients of products for control of crop and lawn pests and diseases, animal ectoparasites, and other pests in public health. The term also includes plant growth regulators, pest repellants, synergists, herbicide safeners (which reduce the phytotoxicity of herbicides to crop plants) and preservatives, the delivery of which to the target may expose dermal and especially ocular tissue to the pesticide. Such exposure can arise by drift of the pesticide from the delivery means to the person performing the application of the pesticide or being present in the vicinity of an application.

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants. The herbicidal effectiveness data set forth herein report "control" as a percentage following a standard procedure in the art which reflects a visual assessment of plant mortality and growth reduction by comparison with untreated plants, made by technicians specially trained to make and record such observations. In all cases, a single technician makes all assessments of percent control within any one experiment or trial. Such measurements are relied upon and regularly reported by Monsanto Company in the course of its herbicide business.

EXAMPLES

The following Examples are provided for illustrative purposes only and are not intended to limit the scope of the present invention. The Examples will permit better under- Section 1

Formulations

Aqueous herbicide formulations were generated from commercially available glyphosate isopropylamine, triclopyr triethylamine and various surfactants in the ratios indicated in Tables 1.1 and 1.2.

TABLE 1.1

Formulations:

| CODE | Glyphosate (G); g ae/L [a] | Triclopyr (T); g ae/L [a] | G:T w:w [b] | Surfactant | Surf w/v % [c] | G:surf w:w [d] |
|---|---|---|---|---|---|---|
| RUP1 | 351 ae (30.6%) | | | FS1 | 11.9 | 3.0 |
| RUP2 | 443 ae (37.2%) | | | FS1 | 9.81 | 4.5 |
| RU1 | 27% Roundup | | | FS4 | 4.11 | 3.5 |
| FG1 | 46.3% ae | | | | | |
| F2M | 142 | 7.71 | 18.5:1 | FS1 | 4.11 | 3.5 |
| F1M | 142 | 3.85 | 18.5:0.5 | FS1 | 4.11 | 3.5 |
| F1C | 142 | 3.85 | 18.5:0.5 | FS4 | 5.4 | 3.6 |
| F2C | 142 | 7.66 | 18.5:1 | FS4 | 5.3 | 3.6 |
| F3M | 143 | 15.4 | 18.6:2 | FS1 | 4.11 | 3.5 |
| F5M | 7.38 | 0.72 | 20.5:2 | FS1 | 0.21 | 3.6 |
| F4C | 151.3 | 24.48 | 18.5:3 | FS4 | 5.7 | 3.6 |
| F11M | 7.38 | 0.36 | 20.5:1 | FS1 | 0.21 | 3.6 |
| F8M | 142 | 92.5 | 18.5:12 | FS1 | 4.11 | 3.5 |
| F9M | 142 | 61.7 | 18.5:8 | FS1 | 4.11 | 3.5 |
| F10M | 142 | 40.9 | 18.5:5.3 | FS1 | 4.11 | 3.5 |

[a] Glyphosate and triclopyr are expressed as the acid equivalent load (g ae/L). The densities of the concentrate formulations are in the range 1.06 to 1.17 g/ml. The ready-to-use formulation has a density of approx. 1.004 g/ml.
[b] The glyphosate/triclopyr w/w ratio given in terms of the acid equivalent weights.
[c] The surfactant load is expressed as the weight/volume %, i.e. g/100 ml.
[d] The glyphosate/surfactant w/w ratio, i.e., g ae/g surfactant per kg of formulation.

TABLE 1.2

Formulations.

| CODE | Glyphosate (G); g/Kg (62% ai) [a] | Triclopyr (T); g/Kg; (44% ai) [b] | G:T w:w [c] | Surfactant | w/w; % [d] |
|---|---|---|---|---|---|
| F14X | 290.3 | 25.5 | 18:1.13 | FS3 | 5 |
| F13X | 290.3 | 51 | 18:2.25 | FS3 | 5 |
| F12X | 290.3 | 101 | 18:4.50 | FS3 | 5 |
| F6X | 290.4 | 60 | 18:2.66 | FS3 | 5 |
| F4X | 290.4 | 67.6 | 18:3 | FS3 | 5 |
| F3X | 290.3 | 45 | 18:2 | FS3 | 5 |
| F2X | 290.3 | 22.5 | 18:1 | FS3 | 5 |
| F1X | 290.3 | 11.3 | 18:0.5 | FS3 | 5 |
| F0X | 290.3 | 0 | 18:0 | FS3 | 5 |
| F14M | 290.3 | 25.5 | 18:1.13 | FS1 | 5 |
| F13M | 290.3 | 51 | 18:2.25 | FS1 | 5 |
| F12M | 290.3 | 101 | 18:4.50 | FS1 | 5 |
| F6M | 290.4 | 60 | 18:2.66 | FS1 | 5 |
| F4M | 290.4 | 67.6 | 18:3 | FS1 | 5 |
| F5M | 16.1 | 2.3 | 1:0.1 | FS1 | 5 |
| F3M | 290.3 | 45 | 18:2 | FS1 | 5 |
| F2M | 290.3 | 22.5 | 18:1 | FS1 | 5 |
| F1M | 290.3 | 11.3 | 18:0.5 | FS1 | 5 |
| F0M | 290.3 | 0 | 18:0 | FS1 | 5 |
| F15C | 290.3 | 152.2 | 18:6.76 | FS4 | 5 |
| F14C | 290.3 | 25.5 | 18:1.13 | FS4 | 5 |
| F13C | 290.3 | 51 | 18:2.25 | FS4 | 5 |
| F12C | 290.3 | 101 | 18:4.50 | FS4 | 5 |
| F4C | 290.3 | 67.6 | 18:3 | FS4 | 5 |
| F3C | 290.3 | 45 | 18:2 | FS4 | 5 |
| F2C | 290.3 | 22.5 | 18:1 | FS4 | 5 |
| F1C | 290.3 | 11.3 | 18:0.5 | FS4 | 5 |
| F0C | 290.3 | 0 | 18:0 | FS4 | 5 |
| F6Y | 290.3 | 59.9 | 18:2.66 | FS5 | 3.5 |
| F3Y | 290.3 | 45 | 18.2 | FS5 | 3.5 |
| F4Y | 290.3 | 67.6 | 18:3 | FS5 | 3.5 |
| F7Y | 290.3 | 90.1 | 18:4 | FS5 | 3.5 |

[a] Glyphosate load expressed as the weight of a standard (62% ai glyphosate) used per 1000 g. The densities of the concentrate formulations are in the range 1.06 to 1.17 g/ml. The ready-to-use formulation has a density of approx. 1.004 g/ml.
[b] Triclopyr load expressed as the weight of a standard (44.3% ai triclopyr) used per 1000 g. The densities of the concentrate formulations are in the range 1.06 to 1.17 g/ml. The ready-to-use formulation has a density of approx. 1.004 g/ml.
[c] The glyphosate/triclopyr w/w ratio is given in terms of the % ai/% ai.
[d] The surfactant is expressed as the w/w % i.e., weight of surfactant standard per 100 g.

Key to Surfactants:

1. FS1 surfactant composition is a mixture of tallowamines and phosphate esters, as described in U.S. Pat. No. 5,703,015.

2. FS2 surfactant composition is a mixture of tallowamines and phosphate esters, as described in U.S. Pat. No. 5,703,015.

3. FS3 surfactant composition is a mixture of a tallowamine ethoxylate with other surfactants.

4. FS4 is a Cocoamine 5EO.

5. FS5 is a Cocoamine 5EO.

Section 2

Stability Test & Results

Example 2.1

Stability Test

Materials & Methods:
Various formulations were maintained at constant temperature for a fixed period and monitored for changes in color, homogeneity and appearance after thawing. The formulations were also cycled through temperature extremes i.e., at low temperatures of −20° C. and −5° C. for the fixed period then raised to the higher temperatures of 20° C. and 5° C. respectively and changes monitored. Results for a 4-week study are tabulated below.

Results:

TABLE 2.1A

Stability Results.

| Formulation CODE | % wt ai Glyphosate | % wt ai Triclopyr | Surfactant (5%) | RT | −20/+20 ° C. (−19.9° C.) | −5/+5° C. (−6.7° C.) | 4.5° C. | 60° C. | −10° C. | Apperance after thawing to Room Temp. |
|---|---|---|---|---|---|---|---|---|---|---|
| F12X | 18 | 4.50 | FS3 | No change | Color at bottom | No change | No change | No change | Solid, crystals | No crystals, homogenous after mixing |
| F13X | 18 | 2.25 | FS3 | No change | Color at bottom | No change | No change | No change | Solid, crystals | No crystals, homogenous after mixing |
| F14X | 18 | 1.13 | FS3 | No change | Color at bottom | No change | No change | No change | Solid, crystals | No crystals, homogenous after mixing |
| F0X | 18 | 0.00 | FS3 | No change | Color at bottom | No change | No change | No change | Solid, crystals | No crystals, homogenous after mixing |
| F12M | 18 | 4.50 | FS1 | No change | X'tals 10% (btm) | No change | No change | No change | Solid, crystals | Crystals remain on bottom (10%) |
| F13M | 18 | 2.25 | FS1 | No change | Color at bottom | No change | No change | No change | Solid, crystals | No crystals, homogenous after mixing |
| F14M | 18 | 1.13 | FS1 | No change | Color at bottom | No change | No change | No change | Solid, crystals | No crystals, homogenous after mixing |
| F0M | 18 | 0.00 | FS1 | No change | Color at bottom | No change | No change | No change | Solid, crystals | No crystals, homogenous after mixing |
| F15C | 18 | 6.76 | FS4 | No change | Color at bottom | No change | No change | No change | Solid, crystals | No crystals, homogenous after mixing |
| F12C | 18 | 4.50 | FS4 | No change | Color at bottom | No change | No change | No change | Solid, crystals | No crystals, homogenous after mixing |
| F13C | 18 | 2.25 | FS4 | No change | Color at bottom | No change | No change | No change | Solid, crystals | No crystals, homogenous after mixing |
| F14C | 18 | 1.13 | FS4 | No change | Color at bottom | No change | No change | No change | Solid, crystals | No crystals, homogenous after mixing |
| F0M | 18 | 0.00 | FS3 | No change | Color at bottom | No change | No change | No change | Solid, crystals | No crystals, homogenous after mixing |

TABLE 2.1B

Stability Results.

| CODE | % wt ai Triclopyr | Surfactant | −20/+20° C. | | 60° C. |
|---|---|---|---|---|---|
| F6X | 2.66 | FS3 | crystals | All formulations layered from freeze thaw | No layering |
| F3X | 2 | FS3 | clear | All formulations layered from freeze thaw | No layering |
| F4X | 3 | FS3 | crystals | All formulations layered from freeze thaw | No layering |
| F6M | 2.66 | FS1 | crystals | All formulations layered from freeze thaw | No layering |
| F3M | 2 | FS1 | clear | All formulations | No |

TABLE 2.1B-continued

Stability Results.

| CODE | % wt ai Triclopyr | Surfactant | −20/+20° C. | | 60° C. |
|---|---|---|---|---|---|
| | | | | layered from freeze thaw | layering |
| F4M | 3 | FS1 | crystals | All formulations layered from freeze thaw | No layering |
| F6Y | 2.66 | FS5 | clear | All formulations layered from freeze thaw | No layering |
| F3Y | 2 | FS5 | clear | All formulations layered from freeze thaw | No layering |
| F4Y | 3 | FS5 | clear | All formulations layered from freeze thaw | No layering |
| F7Z | 4 | FS5 + NMP | crystals | All formulations layered from freeze thaw | No layering |

Section 3

Greenhouse Test & Results

Objective: Greenhouse study of potential Roundup Brushkiller formulations on Red Maple and Red Oak.

Materials & Methods: Standard post emerge herbicide application procedures were used, such the procedure described below. The herbicide formulations tested are listed in Table 3.1 below. Additional information is available in Tables 1.1 and 1.2.

Seeds of the plant species indicated were planted in 3.5 in square pots in a soil mix which was previously steam sterilized and prefertilized with a 14-14-14 NPK slow release fertilizer at a rate of 100 g/ft$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 21° C. during the night. Plants were sub-irrigated throughout the test to ensure adequate soil moisture levels.

Pots were assigned to different treatments in a randomized experimental design with 6 replications. A set of pots was left untreated as a reference against which effects of the treatments could later be evaluated.

Application of glyphosate compositions was made by spraying with a track sprayer fitted with a flateven 8008E nozzle calibrated to deliver a spray volume of 1348 liters per hectare (l/ha) at a pressure of 165 kilopascals (kPa). After treatment, pots were returned to the greenhouse until ready for evaluation. Treatments were made using dilute aqueous compositions.

For evaluation of herbicidal effectiveness, all plants in the test were examined by a single practiced technician, who recorded percent control, a visual measurement of the effectiveness of each treatment by comparison with untreated plants. Control of 0% indicates no effect, and control of 100% indicates that all of the plants are completely dead. Control of 85% or more is in most cases considered acceptable for normal herbicide use; however in greenhouse tests such as those for the examples it is normal to apply compositions at rates which give less than 85% control, as this makes it easier to discriminate among compositions having different levels of effectiveness. The reported % control values represent the average for all replicates of each treatment.

TABLE 3.1

Glyphosate Formulations for Greenhouse Testing:

| Formulation Code | w/w % Glyph. ae | w/w % Glyph. ai | Amt., g ae/L | Salt Form | Surfact. | Amt surfact. w/w % | Other active; Triclopyr | Triclopyr amt % ai |
|---|---|---|---|---|---|---|---|---|
| F3X | 13.34 | 18.00 | 143.70 | IPA | FS3 | 5.0% | Hammer | 2.0% |
| F2X | 13.34 | 18.00 | 143.27 | IPA | FS3 | 5.0% | Hammer | 1.0% |
| F1X | 13.34 | 18.00 | 143.07 | IPA | FS3 | 5.0% | Hammer | 0.5% |
| F0X | 13.34 | 18.00 | 142.78 | IPA | FS3 | 5.0% | | |
| F3M | 13.34 | 18.00 | 143.60 | IPA | FS1 | 5.0% | Hammer | 2.0% |
| F2M | 13.34 | 18.00 | 143.18 | IPA | FS1 | 5.0% | Hammer | 1.0% |
| F1M | 13.34 | 18.00 | 142.96 | IPA | FS1 | 5.0% | Hammer | 0.5% |
| F0M | 13.34 | 18.00 | 142.75 | IPA | FS1 | 5.0% | | |
| F4C | 13.34 | 18.00 | 143.69 | IPA | FS4 | 5.0% | Hammer | 3.0% |
| F3C | 13.34 | 18.00 | 143.26 | IPA | FS4 | 5.0% | Hammer | 2.0% |
| F2C | 13.34 | 18.00 | 142.84 | IPA | FS4 | 5.0% | Hammer | 1.0% |
| F1C | 13.34 | 18.00 | 142.63 | IPA | FS4 | 5.0% | Hammer | 0.5% |
| F0C | 13.34 | 18.00 | 142.83 | IPA | FS4 | 5.0% | | |

| COMMERCIAL PRODUCTS | ACTIVE | % Ai |
|---|---|---|
| RUP BSK CONC | GLYPH | 27.0 |
| BBG | TRICL | 8.0 |
| ENF BSK CONC | TRICL | 8.8 |

Results:

TABLE 3.2A

GREENHOUSE STUDY OF POTENTIAL ROUNDUP BRUSHKILLER
FORMULATIONS ON RED MAPLE AND RED OAK

| | | | | | % CTRL 5 DAT | | | % CTRL 5 DAT | | |
|---|---|---|---|---|---|---|---|---|---|---|
| TRT | CHEMICAL FORMULN | FORM DESIG | MIX RATE OZ/GAL | MAPLE REP 1 | MAPLE REP 2 | MAPLE REP 3 | MAPLE AVE. | OAK REP 1 | OAK REP 2 | OAK AVE. |
| 1 | F3X | SL | 6 | 55.0 | 30.0 | 65.0 | 50.0 | 0.0 | 30.0 | 15.0 |
| 2 | F2X | SL | 6 | 30.0 | 20.0 | 40.0 | 30.0 | 0.0 | 40.0 | 20.0 |
| 3 | F1X | SL | 6 | 20.0 | 50.0 | 20.0 | 30.0 | 45.0 | 70.0 | 57.5 |
| 4 | F0X | SL | 6 | 5.0 | 5.0 | 10.0 | 6.7 | 5.0 | 5.0 | 5.0 |
| 5 | F3M | SL | 6 | 55.0 | 70.0 | 70.0 | 65.0 | 45.0 | 10.0 | 27.5 |
| 6 | F2M | SL | 6 | 25.0 | 35.0 | 70.0 | 43.3 | 10.0 | 10.0 | 10.0 |
| 7 | F1M | SL | 6 | 30.0 | 50.0 | 25.0 | 35.0 | 5.0 | 30.0 | 17.5 |
| 8 | F0M | SL | 6 | 40.0 | 35.0 | 30.0 | 35.0 | 5.0 | 20.0 | 12.5 |
| 9 | F4C | SL | 6 | 55.0 | 55.0 | 65.0 | 58.3 | 80.0 | 10.0 | 45.0 |
| 10 | F3C | SL | 6 | 55.0 | 55.0 | 40.0 | 50.0 | 5.0 | 20.0 | 12.5 |
| 11 | F2C | SL | 6 | 40.0 | 50.0 | 35.0 | 41.7 | 75.0 | 5.0 | 40.0 |
| 12 | F1C | SL | 6 | 35.0 | 35.0 | 20.0 | 30.0 | 5.0 | 10.0 | 7.5 |
| 13 | F0C | SL | 6 | 15.0 | 5.0 | 10.0 | 10.0 | 0.0 | 5.0 | 2.5 |
| 14 | RUP BSK CONC | SL | 6 | 30.0 | 25.0 | 30.0 | 28.3 | 0.0 | 70.0 | 35.0 |
| 15 | ORTHO BBG | SL | 4 | 60.0 | 75.0 | 20.0 | 51.7 | 45.0 | 50.0 | 47.5 |
| 16 | ENF BSK CONC | SL | 4 | 25.0 | 25.0 | 30.0 | 26.7 | 10.0 | 5.0 | 7.5 |
| 17 | UNTREATED CONTROL | | | 0.0 | 0.0 | 0.0 | 0.0 | 0.0 | 0.0 | 0.0 |

TABLE 3.2B

GREENHOUSE STUDY OF POTENTIAL ROUNDUP BRUSHKILLER
FORMULATIONS ON RED MAPLE AND RED OAK

| | | | | | % CTRL 21 DAT | | | % CTRL 21 DAT | | |
|---|---|---|---|---|---|---|---|---|---|---|
| TRT | CHEMICAL FORMULN | FORM DESIG | MIX RATE OZ/GAL | MAPLE REP 1 | MAPLE REP 2 | MAPLE REP 3 | MAPLE AVE. | OAK REP 1 | OAK REP 2 | OAK AVE. |
| 1 | F3X | SL | 6 | 100.0 | 100.0 | 100.0 | 100.0 | 95.0 | 100.0 | 97.5 |
| 2 | F2X | SL | 6 | 100.0 | 100.0 | 100.0 | 100.0 | 100.0 | 100.0 | 100.0 |
| 3 | F1X | SL | 6 | 100.0 | 100.0 | 100.0 | 100.0 | 100.0 | 100.0 | 100.0 |
| 4 | F0X | SL | 6 | 100.0 | 100.0 | 100.0 0 | 100.0 | 80.0 | 100.0 | 90.0 |
| 5 | F3M | SL | 6 | 100.0 | 100.0 | 100.0 | 100.0 | 80.0.0 | 100.0 | 90.0 |
| 6 | F2M | SL | 6 | 100.0 | 100.0 | 100.0 | 100.0 | 95.0 | 95.0 | 95.0 |
| 7 | F1M | SL | 6 | 100.0 | 100.0 | 100.0 | 100.0 | 99.0 | 99.0 | 99.0 |
| 8 | F0M | SL | 6 | 100.0 | 100.0 | 100.0 | 100.0 | 75.0 | 88.0 | 81.5 |
| 9 | F4C | SL | 6 | 100.0 | 100.0 | 100.0 0 | 100.0 | 88.0 | 100.0 | 94.0 |
| 10 | F3C | SL | 6 | 100.0 | 100.0 0 | 100.0.0 | 100.0 | 90.0 | 100.0 | 95.0 |
| 11 | F2C | SL | 6 | 100.0 | 100.0 0 | 100.0 | 100.0 | 100.0 | 98.0 | 99.0 |
| 12 | F1C | SL | 6 | 100.0 | 100.0 | 100.0 | 100.0 | 99.0 | 99.0 | 99.0 |
| 13 | F0C | SL | 6 | 100.0 | 95.0 | 88.0 | 94.3 | 45.0 | 100.0 | 72.5 |
| 14 | RUP BSK CONC | SL | 6 | 100.0 | 100.0 | 100.0 | 100.0 | 100.0 | 95.0 | 97.5 |
| 15 | ORTHO BBG | SL | 4 | 100.0 | 100.0 | 100.0 | 100.0 | 100.0.0 | 100.0 | 100.0 |
| 16 | ENF BSK CONC | SL | 4 | 100.0 | 100.0 | 100.0 | 100.0 | 100.0 | 100.0 | 100.0 |
| 17 | UNTREATED CONTROL | | | 0.0 | 0.0 | 0.0 | 0.0 | 0.0 | 0.0 | 0.0 |

Discussion:

5 DAT: The maples exhibited more injury as the triclopyr level went up. The oaks responded more inconsistently than the maples in this regard. Formulation F1X provided the best control of oak at this rating. Only formulations F3M and F4C provided more injury than Ortho Brush-B-Gone (BBG) on maple. The surfactant FS4 proved to be slightly better overall than did the tallowamine formulation FS1. The other tallowamine FS3 was consistently weaker than both other surfactants.

The current Roundup 27% brushkiller formulation failed to provide the same level of injury as that of the Brush-B-Gone product. It did, however, outperform Enforcer (ENF) on both species.

21 DAT: The maples proved to be much easier to control than the oaks at this evaluation time. Only F0C (no triclopyr) failed to provide 100% control. The oak control went up as the triclopyr level decreased. The lowest level of triclopyr was the best on oak and all triclopyr-containing formulations appeared to perform better than glyphosate alone. Tallowamine formulation FS3 seemed to be the best surfactant on oak.

Sections 4/5

Field Test & Results

Example 4.1

Objective: Demonstrate that F3M and F5M formulations provide commercially acceptable weed control.

Materials and Methods: A Ready-To-Use F5M and concentrate F3M brush killer formulations were evaluated. F5M RTU is constructed as 1% glyphosate, isopropylamine salt and 0.10% triclopyr, triethylamine salt, while F3M concentration formulation is constructed as 18% a.i. glyphosate and 2% a.i. triclopyr.

Nine field trials were conducted at various geographic regions in the U.S. to evaluate poison ivy, poison oak, kudzu, and multiflora rose control when treated with F5M and F3M.

TABLE 4.1.1

Location and Number of Brush Tests by Species.

| Geographic Region | State | Primary Species Tested | | | |
|---|---|---|---|---|---|
| | | Poison Ivy | Poison Oak | Multiflora Rose | Kudzu |
| | | Number of tests | | | |
| Mid-West | Illinois | 1 | | 1 | |
| | Ohio | 1 | | | |
| Central | Missouri | 1 | | | |
| South | Alabama | | | 1 | 1 |
| | Mississippi | 1 | | | 1 |
| West | California | | 1 | | |

The brush tests were conducted on preexisting brush infestations typically located along and within fence and tree lines during June through August. All brush species were well-established and exhibiting complete foliation of leaf tissue at the time of treatment.

Each test was established using a randomized complete block design (RCBD) with each of the formulations being applied to 3, 15 ft$^2$ plots. Equal volumes of formulation were applied to each plot either with a RTU Pull n' Spray® sprayer used to apply, the RTU F5M formulation a Roundup® Herbicide Sprayer to apply the concentrate F3M formulation. F5M was applied based on 1 gal of solution treats 300 sq ft (equivalent to 145 gallons per acre) and the standard application volume for a spray to wet treatment. F3M concentrate formulation was applied at a rate of 6 oz/gallon spray to wet.

Brush control ratings were evaluated at 1, 3, 21 and 90 days after treatment (DAT). Visual assessment of formulation efficacy was assessed on a 0 to 100% scale based on brush control (chorosis, necrosis and kill) compared to the untreated plots. Values close to 0% indicate no visual presence of brush damage by a formulation, while values approaching 100% indicate complete kill of a brush species compared to untreated plots. In addition, values greater than 80% control indicate that a product is supplying the industry standard commercially acceptable weed/brush control.

To quantify differences in percent brush control among formulations for each weed species by observation date, Duncan's multiple range test was applied and evaluated at P=0.05.

Results:

TABLE 4.1.2

F3M and F5M gave commercial control up to 90 DAT on Poison Ivy and Poison Oak.

| | | Poison Ivy | | | | | Poison Oak | | | | |
|---|---|---|---|---|---|---|---|---|---|---|---|
| | | DAT | | | | | | | | | |
| Trt. | Formuln. | 1 | 3 | 7 | 21 | 90 | 1 | 3 | 7 | 21 | 90 |
| | | % Control | | | | | | | | | |
| 1 | F3M | 6a | 36a | 94b | 100a | 100a | 0a | 10b | 85a | 100a | 100a |
| 2 | F5M | 7a | 36a | 96a | 100a | 100a | 0a | 23a | 80b | 100a | 100a |
| 3 | Untreated Check | 0b | 0b | 0c | 0b | 0b | 0a | 0c | 0c | 0b | 0b |

Means followed by same letter, for each weed species, do not significantly differ (P = 0.05, Duncan's multiple range test)

TABLE 4.1.3

F3M and F5M gave commercial control up to 90 DAT on Multiflora Rose and Kudzu.

| | | Multiflora Rose | | | | | Kudzu | | | | |
|---|---|---|---|---|---|---|---|---|---|---|---|
| | | DAT | | | | | | | | | |
| Trt. | Formuln. | 1 | 3 | 7 | 21 | 90 | 1 | 3 | 7 | 21 | 90 |
| | | % Control | | | | | | | | | |
| 1 | F3M | 6a | 34a | 78a | 93a | 100a | 11a | 42b | 70b | 90a | 88a |
| 2 | F5M | 6a | 46b | 80a | 94a | 100a | 10a | 45a | 85a | 93a | 90a |
| 3 | Untreated Check | 0b | 0c | 0b | 0b | 0b | 0b | 0c | 0c | 0b | 0b |

Means followed by same letter, for each weed species, do not significantly differ (P = 0.05, Duncan's multiple range test)

TABLE 4.1.4

F3M and F5M gave commercial control up to 90 DAT on all brush tests combined.

| Trt. | Formuln. | Overall Brush[1] DAT | | | | |
|---|---|---|---|---|---|---|
| | | 1 | 3 | 7 | 21 | 90 |
| | | % Control | | | | |
| 1 | F3M | 6a | 34b | 86a | 96a | 98a |
| 2 | F5M | 7a | 39a | 90a | 97a | 98a |
| 3 | Untreated Chk | 0b | 0c | 0b | 0b | 0b |

[1]Four brush species were tested poison oak, poison ivy, multiflora rose, and kudzu across 9 brush tests
Means followed by same letter, for each weed species, do not significantly differ (P = 0.05, Duncan's multiple range test)

Discussion:
F5M and F3M provided commercial control of tough to control brush. At 90 DAT brush control for all species tested ranged between 90 and 100% control (Tables 4.2.1 through 4.3.4). F5M and F3M tested at various regions and brush species will deliver effective weed control of unwanted vegetation up to 90DAT.

Example 4.2

Evaluation on Poison Ivy

Objectives: Evaluate various formulations on Poison Ivy.
Materials & Methods: Formulations tabulated below were field tested for 14 days in September to October at Clemson, S.C. See Tables 1.1 and 1.2 for description of product formulations.
Results:

TABLE 4.2.1

| Product Form. | Rate in oz/1 gallon | % injury 14 DAT Poison ivy |
|---|---|---|
| 1. BSK | 6 oz | 80 |
| 2. F1M | 6 oz | 80 |
| 3. F2M | 6 oz | 91.6 |
| 4. F4C | 6 oz | 100 |
| 5. F3M | 6 oz | 100 |
| 6. BBG | 4 oz | 70 |
| 7. BBG + FS1 | 4 oz + 3 oz | 86.4 |
| 8. Untreated Check | 0 | 10* |

*Untreated Check displayed some natural yellowing due to senescence, or aging.

Example 4.3

Evaluation on Kudzu

Materials & Methods: Field evaluations of experimental formulations tabulated below were conducted on brush species (Kudzu Roadside) in Mississippi.

TABLE 4.3.1

| Formulation Code | % ai Gly IPA | % ai Triclopyr TEA | Surfactant | % Surfactant |
|---|---|---|---|---|
| F2M | 18 | 1 | FS1 | 5 |
| F1M | 18 | 0.5 | FS1 | 5 |
| F1C | 18 | 0.5 | FS4 | 5 |
| F2C | 18 | 1 | FS4 | 5 |
| F3M | 18 | 2 | FS1 | 5 |
| F4C | 18 | 3 | FS4 | 5 |
| BSK or RU1 | 27 | 0 | FS1 | ? |
| BBG | 0 | | | 0 |

Results:

TABLE 4.3.2

| Trt # | Form Code | Rate fl oz/gal | 7 DAT** | 10 DAT** | 30 DAT** |
|---|---|---|---|---|---|
| 1 | BSK | 6 | 41.7 | 83.3 | 100 |
| 2 | F1M | 6 | 36.7 | 80 | 100 |
| 3 | F2M | 6 | 45 | 87 | 100 |
| 4 | F4C | 6 | 46.7 | 78.3 | 100 |
| 5 | F3M | 6 | 36.7 | 73.3 | 98.3 |
| 6 | BBG | 4 | 33.3 | 23.3 | 73.3 |
| 7 | BBG + FS1 | 43 | 40 | 30 | 85 |
| 8 | Untreated Check | | 0 | 0 | 0 |

**Tabulated values are the mean of 3 tests.

Example 4.4

Field Test at Mississippi #2

Materials & Methods: Evaluations on experimental formulations were conducted on brush species at various locations and summarized below (St Louis, Clemson S.C., Mississippi).
Results:

TABLE 4.4.1

Summary of Brush Tests

| Location | Date First Rated | Formln Code | Formln | DAT | | | | | | | Weed |
|---|---|---|---|---|---|---|---|---|---|---|---|
| | | | | 5 | 7 | 10 | 14 | 16 | 30 | 42 | |
| St Louis | July | F3M | 18 + 2 | 90 | | | | 100 | | 100 | Poison Ivy |
| St Louis | July | F2M | 18 + 1 | 80 | | | | 100 | | 100 | Poison Ivy |
| St Louis | July | F1M | 18 + 0.5 | 70 | | | | 100 | | 100 | Poison Ivy |
| St Louis | July | F4C | 18 + 3 | 95 | | | | 100 | | 100 | Poison Ivy |
| St Louis | July | RU1 | 27% R'up Brush | 50 | | | | 95 | | 100 | Poison Ivy |
| St Louis | July | BBG | Brush-B-Gone | 85 | | | | 100 | | 100 | Poison Ivy |
| St Louis | July | ENF | Enforcer | 85 | | | | 100 | | 100 | Poison Ivy |
| St Louis | July | F3M | 18 + 2 | 85 | | | | 100 | | 100 | Fesc/Blue |
| St Louis | July | F2M | 18 + 1 | 80 | | | | 100 | | 100 | Fesc/Blue |
| St Louis | July | F1M | 18 + 0.5 | 85 | | | | 100 | | 100 | Fesc/Blue |

TABLE 4.4.1-continued

Summary of Brush Tests

| Location | Date First Rated | Formln Code | Formln | 5 | 7 | 10 | 14 | 16 | 30 | 42 | Weed |
|---|---|---|---|---|---|---|---|---|---|---|---|
| St Louis | July | F4C | 18 + 3 | 90 | | | | 100 | | 100 | Fesc/Blue |
| St Louis | July | RU1 | 27% R'up Brush | 50 | | | | 95 | | 100 | Fesc/Blue |
| St Louis | July | BBG | Brush-B-Gon | 50 | | | | 65 | | 70 | Fesc/Blue |
| St Louis | July | ENF | Enforcer | 20 | | | | 15 | | 0 | Fesc/Blue |
| St Louis | July | F3M | 18 + 2 | 80 | | | | 98 | | 100 | Golden Rod |
| St Louis | July | F2M | 18 + 1 | 65 | | | | 88 | | 98 | Golden Rod |
| St Louis | July | F1M | 18 + 0.5 | 35 | | | | 85 | | 100 | Golden Rod |
| St Louis | July | F4C | 18 + 3 | 90 | | | | 98 | | 98 | Golden Rod |
| St Louis | July | RU1 | 27% R'up Brush | 50 | | | | 95 | | 95 | Golden Rod |
| St Louis | July | BBG | Brush-B-Gon | 40 | | | | 65 | | 65 | Golden Rod |
| St Louis | July | ENF | Enforcer | 30 | | | | 75 | | 75 | Golden Rod |
| St Louis | July | F3M | 18 + 2 | 80 | | | | 100 | | 100 | Fesc/Blue |
| St Louis | July | F2M | 18 + 1 | 70 | | | | 100 | | 100 | Fesc/Blue |
| St Louis | July | F1M | 18 + 0.5 | 50 | | | | 100 | | 100 | Fesc/Blue |
| St Louis | July | F4C | 18 + 3 | 70 | | | | 100 | | 100 | Fesc/Blue |
| St Louis | July | RU1 | 27% R'up Brush | 85 | | | | 98 | | 98 | Fesc/Blue |
| St Louis | July | BG | Brush-B-Gon | 0 | | | | 0 | | 0 | Fesc/Blue |
| St Louis | July | ENF | Enforcer | 0 | | | | 0 | | 0 | Fesc/Blue |
| Miss | October | F3M | 18 + 2 | | | 37 | 73 | | 98 | | Kudzu |
| Miss | October | F2M | 18 + 1 | | | 45 | 87 | | 100 | | Kudzu |
| Miss | October | F1M | 18 + 0.5 | | | 37 | 80 | | 100 | | Kudzu |
| Miss | October | F4C | 18 + 3 | | | 47 | 78 | | 100 | | Kudzu |
| Miss | October | RU1 | 27% R'up Brush | | | 42 | 83 | | 100 | | Kudzu |
| Miss | October | BBG | Brush-B-Gon | | | 33 | 23 | | 73 | | Kudzu |
| Miss | October | BBG + FS1 | Brush-B-Gon+ | | | 40 | 30 | | 85 | | Kudzu |
| Clem | October | RU1 | 27% R'up Brush | | | | | 80 | | | Poison Ivy |
| Clem | October | F1M | 18 + 0.5 | | | | | 80 | | | Poison Ivy |
| Clem | October | F2M | 18 + 1 | | | | | 91.6 | | | Poison Ivy |
| Clem | October | F4C | 18 + 3 | | | | | 100 | | | Poison Ivy |
| Clem | October | BBG | Brush-B-Gon | | | | | 70 | | | Poison Ivy |
| Clem | October | BBG + FS1 | Brush-B-Gon+ | | | | | 86.4 | | | Poison Ivy |
| Clem | October | F3M | 18 + 2 | | | | | 100 | | | Poison Ivy |

TABLE 4.4.2

Grand Brush Test Summary

| Location | Prod Code | Formuln | 5 | 7 | 10 | 14 | 16 | 30 | 42 | Weed |
|---|---|---|---|---|---|---|---|---|---|---|
| St Louis | F1M | 18 + 0.5 | 70 | | | | 100 | | 100 | Poison Ivy |
| St Louis | F1M | 18 + 0.5 | 85 | | | | 100 | | 100 | Fesc/Blue |
| St Louis | F1M | 18 + 0.5 | 35 | | | | 85 | | 100 | Golden Rod |
| St Louis | F1M | 18 + 0.5 | 50 | | | | 100 | | 100 | Fesc/Blue |
| Miss | F1M | 18 + 0.5 | | | 37 | 80 | | 100 | | Kudzu |
| Clem | F1M | 18 + 0.5 | | | | 80 | | | | Poison Ivy |
| | | | 60 | | | | 96.3 | | | |
| St Louis | F2M | 18 + 1 | 80 | | | | 100 | | 100 | Poison Ivy |
| St Louis | F2M | 18 + 1 | 80 | | | | 100 | | 100 | Fesc/Blue |
| St Louis | F2M | 18 + 1 | 65 | | | | 88 | | 98 | Golden Rod |
| St Louis | F2M | 18 + 1 | 70 | | | | 100 | | 100 | Fesc/Blue |
| Miss | F2M | 18 + 1 | | | 45 | 87 | | 100 | | Kudzu |
| Clem | F2M | 18 + 1 | | | | 91.6 | | | | Poison Ivy |
| | | | 74 | | | | 97 | | | |
| St Louis | F3M | 18 + 2 | 90 | | | | 100 | | 100 | Poison Ivy |
| St Louis | F3M | 18 + 2 | 85 | | | | 100 | | 100 | Fesc/Blue |
| St Louis | F3M | 18 + 2 | 80 | | | | 98 | | 100 | Golden Rod |
| St Louis | F3M | 18 + 2 | 80 | | | | 100 | | 100 | Fesc/Blue |
| Miss | F3M | 18 + 2 | | | 37 | 73 | | 98 | | Kudzu |
| Clem | F3M | 18 + 2 | | | | 100 | | | | Poison Ivy |
| | | | 84 | | | | 99.5 | | | |
| St Louis | F4C | 18 + 3 | 95 | | | | 100 | | 100 | Poison Ivy |

TABLE 4.4.2-continued

Grand Brush Test Summary

| | | | | | | | | |
|---|---|---|---|---|---|---|---|---|
| St Louis | F4C | 18 + 3 | 90 | | 100 | | 100 | Fesc/Blue |
| St Louis | F4C | 18 + 3 | 90 | | 98 | | 98 | Golden Rod |
| St Louis | F4C | 18 + 3 | 70 | | 100 | | 100 | Fesc/Blue |
| Miss | F4C | 18 + 3 | | 47 | 78 | | 100 | Kudzu |
| Clem | F4C | 18 + 3 | | | 100 | | | Poison Ivy |
| | | | 86 | | | 99.5 | | |
| St Louis | RU1 | 27% R'up Brush | 50 | | 95 | | 100 | Poison Ivy |
| St Louis | RU1 | 27% R'up Brush | 50 | | 95 | | 100 | Fesc/Blue |
| St Louis | RU1 | 27% R'up Brush | 50 | | 95 | | 95 | Golden Rod |
| St Louis | RU1 | 27% R'up Brush | 85 | | 98 | | 98 | Fesc/Blue |
| Miss | RU1 | 27% R'up Brush | | 42 | 83 | | 100 | Kudzu |
| Clem | RU1 | 27% R'up Brush | | | 80 | | | Poison Ivy |
| | | | 59 | | | 95.8 | | |
| St Louis | BBG | Brush-B-Gon | 85 | | 100 | | 100 | Poison Ivy |
| St Louis | BBG | Brush-B-Gon | 50 | | 65 | | 70 | Fesc/Blue |
| St Louis | BBG | Brush-B-Gon | 40 | | 65 | | 65 | Golden Rod |
| St Louis | BBG | Brush-B-Gone | 0 | | 0 | | 0 | Fesc/Blue |
| Miss | BBG | Brush-B-Gone | | 33 | 23 | | 73 | Kudzu |
| Clem | BG | Brush-B-Gone | | | 70 | | | Poison Ivy |
| | | | 44 | | | 57.5 | | |
| Miss | BBG + FS1 | Brush-B-Gone+ | | 40 | 30 | | 85 | Kudzu |
| Clem | BBG + FS1 | Brush-B-Gone+ | | | 86.4 | | | Poison Ivy |
| St Louis | ENF | Enforcer | 85 | | 100 | | 100 | Poison Ivy |
| St Louis | ENF | Enforcer | 20 | | 15 | | 0 | Fesc/Blue |
| St Louis | ENF | Enforcer | 30 | | 75 | | 75 | Golden Rod |
| St Louis | ENF | Enforcer | 0 | | 0 | | 0 | Fesc/Blue |
| | | | 34 | | | 47.5 | | |

| Product Code | 5 DAT | 7 DAT | 10 DAT | 14 DAT | 16 DAT | 30 DAT | 42 DAT | Weed |
|---|---|---|---|---|---|---|---|---|
| BBG | 85 | | | | 100 | | 100 | Poison Ivy |
| BBG | 50 | | | | 65 | | 70 | Fesc/Blue |
| BBG | 40 | | | | 65 | | 65 | Golden Rod |
| BBG | 0 | | | | 0 | | 0 | Fesc/Blue |
| BBG | | 33 | 23 | | | 73 | | Kudzu |
| BBG | | | | 70 | | | | Poison Ivy |
| RU1 | 50 | | | | 95 | | 100 | Poison Ivy |
| RU1 | 50 | | | | 95 | | 100 | Fesc/Blue |
| RU1 | 50 | | | | 95 | | 95 | Golden Rod |
| RU1 | 85 | | | | 98 | | 98 | Fesc/Blue |
| RU1 | | 42 | 83 | | | 100 | | Kudzu |
| RU1 | | | | 80 | | | | Poison Ivy |
| F3M | 90 | | | | 100 | | 100 | Poison Ivy |
| F3M | 85 | | | | 100 | | 100 | Fesc/Blue |
| F3M | 80 | | | | 98 | | 100 | Golden Rod |
| F3M | 80 | | | | 100 | | 100 | Fesc/Blue |
| F3M | | 37 | 73 | | | 98 | | Kudzu |
| F3M | | | | 100 | | | | Poison Ivy |

Example 5

Additional Field Test in St. Louis

Following the procedures set forth in Example 4, additional fields tests were carried in the St. Louis area in July of 2003, in order to further evaluate the performance of various formulations on poison ivy, as well as all weeds present. (See Tables 1.1, 1.2 and 3 for additional details on product formulations.) The results of these tests are presented in Table 5, below.

TABLE 5

Summary of Test Results

| Formuln Code | Formln | Rate in oz/1 gallon | Poison Ivy % injury 6 DAT | Poison Ivy % injury 12 DAT | Total weed % injury 6 DAT | Total weed % injury 12 DAT |
|---|---|---|---|---|---|---|
| SBK | Super BK 32 | 3.2 | 60 | 90 | 50 | 65 |
| SPC | Spectra conc | 5 | 70 | 94 | 70 | 80 |
| ENF | Enforcer | 2.56 | 65 | 90 | 55 | 60 |
| BBG | Brush-B-Gon | 4 | 60 | 85 | 55 | 60 |
| F3M | 18 + 2 | 6 | 90 | 100 | 90 | 96 |
| F5M | 1 + 0.1 | RTU | 85 | 100 | 85 | 96 |
| RUP | R'up RTU | RTU | 80 | 99 | 80 | 94 |

TABLE 5-continued

Summary of Test Results

| Formuln Code | Formln | Rate in oz/1 gallon | Poison Ivy % injury 6 DAT | Poison Ivy % injury 12 DAT | Total weed % injury 6 DAT | Total weed % injury 12 DAT |
|---|---|---|---|---|---|---|
| RU1 | 27% R'up Brush | 6 | 90 | 90 | 80 | 85 |

What is claimed is:

1. An aqueous herbicidal composition useful for killing or controlling the growth of unwanted plants comprising:
glyphosate or a salt or ester thereof;
triclopyr or a salt or ester thereof; and,
at least one surfactant;
wherein the glyphosate, on an acid equivalent basis, and the triclopyr, on an acid equivalent basis, are present in a weight ratio of from 8:1 to about 20:1, and further wherein when the glyphosate is predominantly in the form of a salt, said salt is selected from the group consisting of a sodium salt, an ammonium salt, an alkylammonium salt, a $C_3$-$C_{16}$ alkanolammonium salt, a di-ammonium salt, an alkylamine salt, a $C_3$-$C_{16}$ alkanolamine salt, an alkylsulfonium salt, a sulfoxonium salt, and combinations thereof.

2. The aqueous herbicidal composition of claim 1 wherein the glyphosate concentration ranges from about 4 grams to about 25 grams acid equivalent per liter.

3. The aqueous herbicidal composition of claim 1 wherein the triclopyr concentration ranges from about 0.4 grams to about 6 grams acid equivalent per liter.

4. The aqueous herbicidal composition of claim 1 wherein the weight ratio (a.e. basis) of glyphosate to triclopyr ranges from about 8:1 to about 15:1.

5. The aqueous herbicidal liquid concentrate of claim 1 wherein the glyphosate concentration ranges from at least about 100 grams to about 400 grams acid equivalent per liter.

6. The aqueous herbicidal liquid concentrate of claim 1 wherein the triclopyr concentration ranges from at least about 8 to about 20 grams acid equivalent per liter.

7. The aqueous herbicidal liquid concentrate of claim 1 wherein the glyphosate concentration ranges from at least about 75 grams to about 160 grams acid equivalent per liter.

8. The aqueous herbicidal composition of claim 1 wherein the triclopyr concentration ranges from about 0.4 grams to about 3 grams acid equivalent per liter.

9. The aqueous herbicidal composition of claim 1 wherein the surfactant concentration is not greater than 9.3 grams per liter.

10. The aqueous herbicidal composition of claim 1 wherein the surfactant concentration is not greater than 6.6 grams per liter.

11. The aqueous herbicidal composition of claim 1 wherein the surfactant concentration is not greater than 3.9 grams per liter.

12. The aqueous herbicidal composition as set forth in claim 1 wherein the glyphosate concentration ranges from about 4 to about 25 grams per liter a.e. and the triclopyr concentration ranges from about 0.4 to about 6 grams per liter a.e.

13. The aqueous composition as set forth in claim 12 wherein the triclopyr concentration ranges from about 0.4 to about 3 grams per liter a.e.

14. The aqueous herbicidal composition as set forth in claim 1 wherein the glyphosate concentration ranges from about 100 to about 400 grams per liter a.e. and the triclopyr concentration ranges from about 8 to about 20 grams per liter a.e.

15. An aqueous herbicidal composition as set forth in claim 1 wherein triclopyr is present in its acid or salt form.

16. A method for killing or controlling the growth of unwanted plants comprising contacting the foliage of said plants with a herbicidally effective amount of the herbicidal composition of claim 1.

17. An aqueous herbicidal composition useful for killing or controlling the growth of unwanted plants comprising:
glyphosate, wherein the glyphosate is predominantly in the form of potassium glyphosate, monoethanolamine glyphosate, or a mixture thereof; and
a pyridine analog selected from the group consisting of triclopyr or a herbicidal derivative thereof;
wherein (i) the glyphosate salt is present in a concentration less than 180 grams acid equivalent per liter and the glyphosate salt (acid equivalent basis) and the pyridine analog (acid equivalent basis) are present in a weight ratio of at least 1:1, glyphosate being in excess; (ii) the glyphosate salt is present in a concentration less than 240 grams acid equivalent per liter and the glyphosate salt (acid equivalent basis) and the pyridine analog (acid equivalent basis) are present in a weight ratio of at least 2:1; (iii) the glyphosate salt is present in a concentration less than 270 grams acid equivalent per liter and the glyphosate salt (acid equivalent basis) and the pyridine analog (acid equivalent basis) are present in a weight ratio of at least 3:1; (iv) the glyphosate salt is present in a concentration less than 288 grams acid equivalent per liter and the glyphosate salt (acid equivalent basis) and the pyridine analog (acid equivalent basis) are present in a weight ratio of at least 4:1; (v) the glyphosate salt is present in a concentration less than 300 grams acid equivalent per liter and the glyphosate salt (acid equivalent basis) and the pyridine analog (acid equivalent basis) are present in a weight ratio of at least 5:1; (vi) the glyphosate salt is present in a concentration less than 308 grams acid equivalent per liter and the glyphosate salt (acid equivalent basis) and the pyridine analog (acid equivalent basis) are present in a weight ratio of at least 6:1; (vii) the glyphosate salt is present in a concentration less than 315 grams acid equivalent per liter and the glyphosate salt (acid equivalent basis) and the pyridine analog (acid equivalent basis) are present in a weight ratio of at least 7:1; (viii) the glyphosate salt is present in a concentration less than 320 grams acid equivalent per liter and the glyphosate salt (acid equivalent basis) and the pyridine analog (acid equivalent basis) are present in a weight ratio of at least 8:1; (ix) the glyphosate salt is present in a concentration less than 324 grams acid equivalent per liter and the glyphosate salt (acid equivalent basis) and the pyridine analog (acid equivalent basis) are present in a weight ratio of at least 9:1; or (x) the glyphosate salt is present in a concentration less than 326 grams acid equivalent per liter and the glyphosate salt (acid equivalent basis) and the pyridine analog (acid equivalent basis) are present in a weight ratio of at least 10:1.

18. The aqueous herbicidal composition of claim 17 wherein the glyphosate concentration ranges from about 4 grams to about 25 grams acid equivalent per liter.

19. The aqueous herbicidal composition of claim 17 wherein the pyridine analog concentration ranges from about 0.8 grams to about 2 grams acid equivalent per liter.

20. The aqueous herbicidal composition of claim 17 wherein the weight ratio (a.e. basis) of glyphosate to pyridine analog is at least about 11:1.

21. The aqueous herbicidal composition of claim 17 wherein the weight ratio (a.e. basis) of glyphosate to pyridine analog is at least about 15:1.

22. The aqueous herbicidal composition of claim 17 further comprising a surfactant.

23. The aqueous herbicidal composition of claim 17 comprising between about 4 and about 25 grams per liter glyphosate a.e. and between about 0.4 and about 6 grams per liter triclopyr a.e.

24. The aqueous herbicidal composition of claim 17 comprising between about 100 and about 400 grams per liter glyphosate a.e. and between about 8 and about 20 grams per liter triclopyr a.e.

25. A method for killing or controlling the growth of unwanted plants comprising contacting the foliage of said plants with a herbicidally effective amount of the herbicidal composition of claim 17.

26. The aqueous herbicidal liquid concentrate of claim 1 or claim 22 wherein said surfactant is selected from the group consisting of:

(a) a secondary or tertiary amine having the formula:

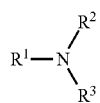
(1)

wherein $R^1$ and $R^2$ are hydrocarbyl having from 1 to about 30 carbon atoms, and $R^3$ is hydrogen or hydrocarbyl having from 1 to about 30 carbon atoms;

(b) a monoalkoxylated amine having the formula:

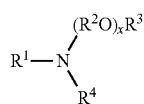
(2)

wherein $R^1$ and $R^4$ are independently hydrocarbyl or substituted hydrocarbyl groups having from 1 to about 30 carbon atoms or $-R^5SR^6$, $R^2$ in each of the x ($R^2O$) groups is independently $C_2$-$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60;

(c) a dialkoxylated quaternary ammonium salt having the formula:

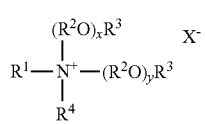
(3)

wherein $R^1$ is hydrocarbyl or substituted hydrocarbyl having from 1 to about 30 carbon atoms, $R^2$ in each of the x ($R^2O$) and y ($R^2O$) groups is independently $C_2$-$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X— is an agriculturally acceptable anion;

(d) a monoalkoxylated quaternary ammonium salt having the formula:

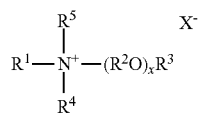
(4)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 30 carbon atoms, x is an average number from 1 to about 60, and X— is an agriculturally acceptable anion;

(e) a quaternary ammonium salt having the formula:

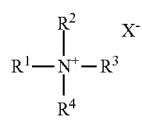
(5)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X— is an agriculturally acceptable anion;

(f) an ether amines having the formula:

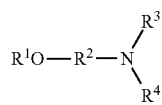
(6)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or $-(R^5O)_xR^6$, $R^5$ in each of the $x(R^5-O)$ groups is independently $C_2$-$C_4$ alkylene, $R^6$ is hydrogen, or a linear or branched alkyl group having from 1 to about 4 carbon atoms, and x is an average number from 1 to about 50;

(g) a diamine having the formula:

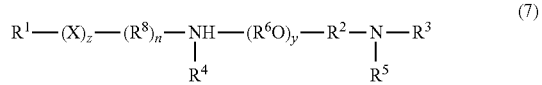
(7)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$; $R^2$ and $R^8$ are independently hydrocarbylene or substituted hydrocarbylene having from 2 to about 30 carbon atoms, $R^6$ in each of the x $(R^6O)$ and y $(R^6O)$ groups is independently $C_2$-$C_4$ alkylene, $R^7$ is hydrogen, or a linear or branched alkyl group having from 1 to about 30 carbon atoms, x is an average number from 1 to about 30, X is —O—, —N($R^6$)—, —C(O)—, —C(O)O—, —OC(O)—, —N($R^9$)C(O)—, —C(O)N($R^9$)—, —S—, —SO—, or —SO$_2$—, y is 0 or an average number from 1 to about 30, n and z are independently 0 or 1, and $R^9$ is hydrogen or hydrocarbyl or substituted hydrocarbyl;

(h) an amine oxide having the formula:

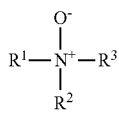
(8)

wherein $R^1$, $R^2$ and $R^3$ are independently hydrogen, hydrocarbyl or substituted hydrocarbyl, —$(R^4O)_xR^5$, or —$R^6(OR^4)_xOR^5$; $R^4$ in each of the x $(R^4O)$ groups is independently $C_2$-$C_4$ alkylene, $R^5$ is hydrogen, or a linear or branched alkyl group having from 1 to about 30 carbon atoms, $R^6$ is hydrocarbylene or substituted hydrocarbylene having from 2 to about 6 carbon atoms, x is an average number from 1 to about 50, and the total number of carbon atoms in $R^1$, $R^2$ and $R^3$ is at least 8;

(i) a dialkoxylated amine having the formula:

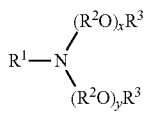
(9)

wherein $R^1$ is a hydrocarbyl or substituted hydrocarbyl having from about 6 to about 30 carbon atoms, or —$R^4SR^5$, $R^4$ and $R^2$ in each of the x $(R^2O)$ and the y $(R^2O)$ groups is independently $C_2$-$C_4$ alkylene, $R^3$ is hydrogen, or a linear or branched alkyl group having from 1 to about 4 carbon atoms, $R^5$ is a linear or branched alkyl group having from about 4 to about 15 carbon atoms, and x and y are independently an average number from 1 to about 40;

(j) an aminated alkoxylated alcohol having the structure:

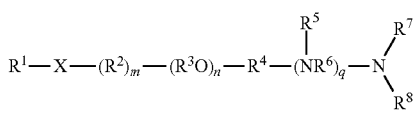
(10)

wherein $R^1$, $R^7$, $R^8$, and $R^9$ are each independently hydrogen, hydrocarbyl or substituted hydrocarbyl having from 1 to about 30 carbon atoms, or —$(R^{11})_s(R^3O)_vR^{10}$; X is —O—, —OC(O)—, —C(O)O—, —N($R^{12}$)C(O)—, —C(O)N($R^{12}$)—, —S—, —SO—, —SO$_2$— or —N($R^9$)—; $R^3$ in each of the n $(R^3O)$ groups and the v $(R^3O)$ groups is independently $C_2$-$C_4$ alkylene; $R^{10}$ is hydrogen, or a linear or branched alkyl group having from 1 to about 30 carbon atoms; n is an average number from 1 to about 60; v is an average number from 1 to about 50; $R^2$ and $R^{11}$ are each independently hydrocarbylene or substituted hydrocarbylene having from 1 to about 6 carbon atoms; $R^4$ is hydrocarbylene or substituted hydrocarbylene having from 2 to about 6 carbon atoms; $R^{12}$ is hydrogen or hydrocarbyl or substituted hydrocarbyl having from 1 to about 30 carbon atoms; m and s are each independently 0 or 1; $R^6$ is hydrocarbylene or substituted hydrocarbylene having from 2 to about 30 carbon atoms, —C(=$NR^{12}$)—, —C(S)—, or —C(O)—; q is an integer from 0 to 5; and $R^5$ is hydrogen or hydrocarbyl or substituted hydrocarbyl having from 1 to about 30 carbon atoms;

(k) a quaternary ammonium, sulfonium and sulfoxonium salt having the formula:

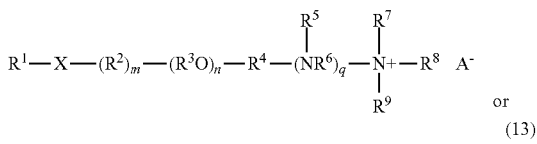
(12)

or

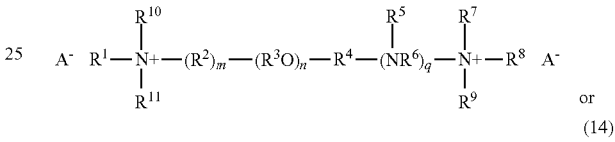
(13)

or

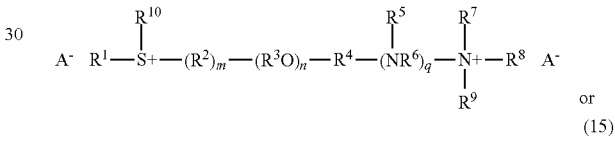
(14)

or

(15)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or —$(R^{13})_s(R^3O)_vR^{12}$; X is —O—, —OC(O)—, —N($R^{14}$)C(O)—, —C(O)N($R^{14}$)—, —C(O)O—, or —S—; $R^3$ in each of the n $(R^3O)$ groups and v $(R^3O)$ groups is independently $C_2$-$C_4$ alkylene; $R^{12}$ is hydrogen, or a linear or branched alkyl group having from 1 to about 30 carbon atoms; n is an average number from 1 to about 60; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, —C(=$NR^{12}$)—, —C(S)—, or —C(O)—; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each $A^-$ is an agriculturally acceptable anion;

(l) a diamine or diammonium salt having the formula:

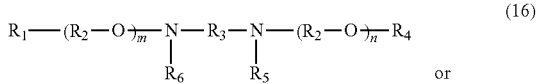
(16)

or

-continued

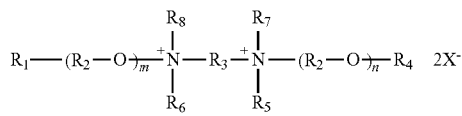
(17)

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m ($R^2O$) and n ($R^2O$) groups and $R^9$ are independently $C_2$-$C_4$ alkylene, $R^3$ is hydrocarbylene or substituted hydrocarbylene having from about 2 to about 6 carbon atoms or $-(R^2O)_pR_9-$, m and n are individually an average number from 0 to about 50, and p is an average number from 0 to about 60;

(m) an alkoxylated alcohol having the formula:

$$R^1O-(R^2O)_xR^3 \quad (18)$$

wherein $R^1$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 4 carbon atoms, and x is an average number from 1 to about 60;

(n) an alkoxylated dialkylphenol having the formula:

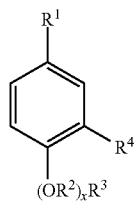
(19)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^2O$) groups is independently $C_2$-$C_4$ alkylene, $R^3$ is hydrogen, or a linear or branched alkyl group having from 1 to about 4 carbon atoms, and x is an average number from 1 to about 60;

(o) an alkyl alkoxylated phosphate having the formula:

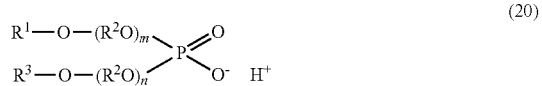
(20)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$-$C_4$ alkylene; and m and n are independently from 1 to about 30;

(p) an alkyl alkoxylated phosphate having the formula:

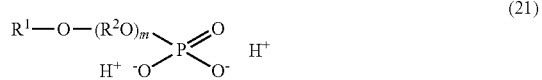
(21)

wherein $R^1$ is a linear or branched alkyl, linear or branched alkenyl, linear or branched alkynyl, aryl, or aralkyl group having from about 8 to about 30 carbon atoms; $R^2$ in each of the m ($R^2O$) groups is independently $C_2$-$C_4$ alkylene; and m is from 1 to about 30;

and mixtures or combinations thereof.

* * * * *